United States Patent
Czaplewski et al.

(10) Patent No.: US 10,160,838 B2
(45) Date of Patent: Dec. 25, 2018

(54) CROSSLINKING MATERIALS FROM BIORENEWABLE ACONITIC ACID

(71) Applicant: International Business Machines Corporation, Armonk, NY (US)

(72) Inventors: Sarah K. Czaplewski, Rochester, MN (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 33 days.

(21) Appl. No.: 15/470,279

(22) Filed: Mar. 27, 2017

(65) Prior Publication Data

US 2018/0273704 A1    Sep. 27, 2018

(51) Int. Cl.
| | |
|---|---|
| C08J 3/24 | (2006.01) |
| C08G 77/38 | (2006.01) |
| C07C 67/10 | (2006.01) |
| C07C 67/02 | (2006.01) |
| C07C 67/00 | (2006.01) |
| C07C 319/12 | (2006.01) |
| C07C 29/147 | (2006.01) |
| C07C 67/08 | (2006.01) |
| C07C 41/01 | (2006.01) |

(52) U.S. Cl.
CPC .............. *C08J 3/24* (2013.01); *C07C 29/147* (2013.01); *C07C 41/01* (2013.01); *C07C 67/00* (2013.01); *C07C 67/02* (2013.01); *C07C 67/08* (2013.01); *C07C 67/10* (2013.01); *C07C 319/12* (2013.01); *C08G 77/38* (2013.01); *C08J 2383/06* (2013.01)

(58) Field of Classification Search
None
See application file for complete search history.

(56) References Cited

U.S. PATENT DOCUMENTS

| | | | |
|---|---|---|---|
| 2,587,295 A | 2/1952 | Doyle et al. | |
| 2,716,638 A * | 8/1955 | Ladd | C07F 7/0849 |
| | | | 174/76 |
| 2,717,900 A | 9/1955 | Plueddemann et al. | |

(Continued)

FOREIGN PATENT DOCUMENTS

| | | |
|---|---|---|
| CN | 105287320 A | 2/2016 |
| CN | 105473126 A | 4/2016 |
| WO | WO-2005/052019 A1 | 6/2005 |

OTHER PUBLICATIONS

Bailey et al. "Pyrolysis of Esters. III. Synthesis of 2-Vinylbutadiene" J. Am. Chem. Soc. 77, 1955, 1133-1136. (Year: 1955).*

(Continued)

*Primary Examiner* — Robert S Loewe
(74) *Attorney, Agent, or Firm* — Roy R. Salvagio; Nathan M. Rau; Kennedy Lenart Spraggins LLP

(57) ABSTRACT

A process includes forming a bio-derived crosslinking material from biorenewable aconitic acid. The process includes initiating a chemical reaction to form a bio-derived crosslinking material that includes multiple functional groups. The chemical reaction includes converting each carboxylic acid group of a biorenewable aconitic acid molecule to one of the multiple functional groups.

16 Claims, 20 Drawing Sheets

(56) References Cited

U.S. PATENT DOCUMENTS

| | | | |
|---|---|---|---|
| 2,813,117 A * | 11/1957 | Roberts | C07C 69/52 560/193 |
| 3,206,415 A | 9/1965 | Horst et al. | |
| 4,045,602 A | 8/1977 | Sommer et al. | |
| 4,301,268 A | 11/1981 | Kropac | |
| 4,474,933 A | 10/1984 | Huber et al. | |
| 4,781,973 A | 11/1988 | Zotto | |
| 4,895,830 A | 1/1990 | Takeda et al. | |
| 5,861,467 A | 1/1999 | Bujanowski et al. | |
| 6,203,923 B1 | 3/2001 | Bansleben et al. | |
| 6,239,204 B1 | 5/2001 | Miura et al. | |
| 6,572,882 B1 | 6/2003 | Vercauteren et al. | |
| 6,605,691 B1 | 8/2003 | Gross et al. | |
| 6,809,231 B2 | 10/2004 | Edwards | |
| 7,670,686 B2 | 3/2010 | Chen et al. | |
| 2003/0149124 A1 | 8/2003 | Thommes et al. | |
| 2011/0217750 A1 | 9/2011 | Pandit et al. | |
| 2012/0184682 A1 | 7/2012 | Dasgupta | |
| 2012/0220749 A1 | 8/2012 | Dasgupta | |
| 2012/0295353 A1 | 11/2012 | Hong et al. | |
| 2013/0272755 A1 | 10/2013 | Takeuchi et al. | |
| 2014/0004251 A1 | 1/2014 | Pandit et al. | |
| 2014/0037772 A1 | 2/2014 | Lien | |
| 2014/0107350 A1 | 4/2014 | Nakamura et al. | |
| 2014/0296425 A1 | 10/2014 | Tew et al. | |
| 2014/0329958 A1 | 11/2014 | Lester et al. | |
| 2014/0355173 A1 | 12/2014 | Odle et al. | |
| 2015/0005247 A1 | 1/2015 | Chen et al. | |
| 2015/0179357 A1 | 6/2015 | Ichinomiya et al. | |
| 2016/0032043 A1 | 2/2016 | von Recum | |
| 2016/0194574 A1 | 7/2016 | Gross et al. | |
| 2016/0284905 A1 | 9/2016 | Mitobe et al. | |
| 2017/0121469 A1 | 5/2017 | Kobilka et al. | |

OTHER PUBLICATIONS

William F. Bruce, "Aconitic Acid" Organic Syntheses, Coll. vol. 2. p. 12 (1943); vol. 17, p. 1 (1937). (Year: 1943).*

Czaplewski et al., Bio-Derived Cross-Linkers, U.S. Appl. No. 15/410,025, International Business Machines, filed Jan. 19, 2017, 22 pages.

King et al., Crosslinkers From Biorenewable Resveratrol, U.S. Appl. No. 15/417,465, International Business Machines, filed Jan. 27, 2017, 21 pages.

Czaplewski et al., Crosslinking Materials From Biorenewable Aconitic Acid, U.S. Appl. No. 15/815,266, International Business Machines, filed Nov. 16, 2017, 37 pages.

King et al., Crosslinkers From Biorenewable Resveratrol, U.S. Appl. No. 15/808,981, International Business Machines, filed Nov. 10, 2017, 21 pages.

Czaplewski et al., Bio-Derived Cross-Linkers, U.S. Appl. No. 15/862,315, International Business Machines, filed Jan. 4, 2018, 22 pages.

AUS920170128US1, Appendix P; List of IBM Patents or Applications Treated as Related, Feb. 20, 2018, 2 pages.

AUS920170128US1, Appendix P; List of IBM Patent or Applications Treated as Related, Jun. 14, 2017, 2 pages.

Haimov, Preparation, Characterization and Catalysis by Polyoxometalate-Synthetic Protein and Polyoxometalate-Protein Hybrid Assemblies, Thesis, Sep. 2007, 93 pages, Weizmann Institute of Science, Rehovot, Israel, URL: https://lib-phds1.weizmann.ac.il/Dissertations/Haimov_Adina.pdf.

Kim et al., Fabrication of PDMS Microlenses With Various Curvatures Using a Water-Based Molding Method, Twelfth International Conference on Miniaturized Systems for Chemistry and Life Sciences, Oct. 2008, pp. 994-996, Royal Society of Chemistry (rsc.org) online, URL: www.rsc.org/binaries/LOC/2008/PDFs/Papers/335_1030.pdf.

Xiameter, An Overview of Polydimethylsiloxane (PDMS) Fluids in the Environment, Product Information, xiameter.com (online), [accessed Nov. 17, 2016], URL: www.xiameter.com/en/ExploreSilicones/Documents/95-725-01%20Overview%20of%20Polydimethylsiloxane%20Fluids.pdf.

Gelest, Functional Silicone Reactivity Guide, Product Brochure, Reactive Silicones: Forging New Polymer Links gelest.com (online), [accessed Nov. 17, 2016], p. 2, URL: www.gelest.com/wp-content/uploads/Goods-PDF-brochures-reactivesilicones.pdf.

Innocentive, Cost-effective, Large-scale Production of Natural Leaf Alcohol (cis-3-hexenol), Product Challenge No. 9933857, innocentive.com (online), [accessed Nov. 17, 2016], 3 pages, URL: www.innocentive.com/ar/challenge/9933857.

Lee et al., Polymer Nanodo-Hybridized Alkyl Silicon Oxide Nanostructures for Organic Memory Transistors with Outstanding High-Temperature Operation Stability, Scientific Reports, 6:33863, DOI: 10.1038/srep33863, <https://www.ncbi.nlm.nih.gov/pmc/articles/PMC5050446/>, Published Oct. 5, 2016, 10 pages.

Gokmen et al., Porous polymer particles—A comprehensive guide to synthesis, characterization, functionalization, and applications, Elsevier, Science Direct, Progress in Polymer Science, vol. 37, Issue 3, < https://webcache.googleusercontent.com/search?q=cache:hbxd4uQY3WAJ:https://pdfs.semanticscholar.org/ed87/e2fd4e12c9c586c31de29d125f3ac5907b72.pdf+&cd=2&hl=en&ct=clnk&gl=us>, Available online Jul. 23, 2011, 41 pages.

Agarwal et al., Use of electrospinning technique for biomedical application, Elsevier, Polymer, vol. 49, Issue 26, < http://www.sciencedirect.com/science/article/pii/S0032386108007994>, dated Dec. 8, 2008, 19 pages.

Schwarz et al., Preparation of molecularly imprinted polymers for the selective recognition of the bioactive polyphenol, (E)-resveratrol, Elsevier, Journal of Chromatography A, vol. 1218, Issue 16, Available Online Feb. 23, 2011, 7 pages.

Zhang et al., Study on the preparation of genipin crosslinked chitosan microspheres of resveratrol and in vitro release, Journal of Polymer Research, (2013) 20:175, Springer Science+Business Media Dordecht 2013, published online Jun. 10, 2013, 10 pages.

Wikipedia, Resveratrol, wikipedia.org (online), accessed Jan. 17, 2017, 18 pages, URL: en.wikipedia.org/wiki/Resveratrol.

Fawcett et al., Phototunable Cross-Linked Polysiloxanes, Macromolecules, vol. 48, No. 18, Sep. 2015, pp. 6499-6507, American Chemical Society (ACS) Publications, Washington, DC.

European Coatings, Renewable Pentaerythritol to Cut Carbon Footprint, European-Coatings.com (online), Jun. 15, 2010, 1 pp., URL: www.european-coatings.com/Raw-materials-technologies/Raw-materials/Coatings.

Anonymous, Cross-Linked Bio-Plasticized Polymer Compositions, An IP.com Prior Art Database Technical Disclosure, IP.com (online), Oct. 17, 2011, 3 pp., URL: ip.com/IPCOM000211763.

Bender Analytical Holding B.V. et al.; Cross-Linked Polymers and Implants Derived from Electrophilically Activated Polyoxazoline, An IP.com Prior Art Database Technical Disclosure, IP.com (online), Mar. 19, 2012, 42 URL: ip.com/IPCOM/000216010.

IBM, IBM Academy of Technology Top 10 Technical Themes 2016, IBM.com (online), accessed Jan. 16, 2017, 2 pages, URL: http://www-03.ibm.com/ibm/academy/tech/tech.shtml.

Dlamini et al., Effect of Cross-Linking Agent Chemistry and Coating Conditions on Physical, Chemical, and Separation Properties of PVA-Psf Composite Membranes, Separation of Science and Technology, vol. 49, Issue 1, Jan. 2014, pp. 22-29, Taylor & Francis Online (tandfonline.com), URL: www.tandfonline.com/doi/full/10.1080/01496395.2013.813040?scroll=top&needAccess=true.

Tang et al., Whiteness improvement of citric acid crosslinked cotton fabrics: H2O2 bleaching under alkaline condition, Carbohydrate Polymers, vol. 147, Aug. 2016, pp. 139-145, PubMed.gov (online), National Center for Biotechnology Information, U.S. National Library of Medicine, Bethesda MD.

Zhao et al., Organic Acids Can Crosslink Poly(ionic liquid)s into Mesoporous Polyelectrolyte Complex, Electronic Supplementary Material (ESI) for Polymer Chemistry, Issue 4, Feb. 2013, pp. 2432-2435, Royal Society of Chemistry, London, UK.

Chemical Processing, Bio-based Route for Allyl Alcohols Beckons, ChemicalProcessing.com (online), Jul. 2009, 5 pages, URL: www.chemicalprocessing.com/articles/2009/150/.

(56) References Cited

OTHER PUBLICATIONS

Sekab, *Chemistry for the Future*, sekab.com (online), [accessed Mar. 9, 2017], 1 page, URL: www.sekab.com/chemistry/.
Holladay et al., *Biorenewable Processes to Acrylic Acid*, Abstract, Pacific Northwest National Laboratory (pnnl.gov) online, [accessed Mar. 9, 2017], 1 page, URL: iic.pnnl.gov/abstracts/nacs/o_109.pdf.
Myriant, *Broad Pipeline, Diverse Applications*, Product Pipeline, myrinat.com (online), [accessed Mar. 9, 2017], 1 page, URL: www.myriant.com/products/product-pipeline.cfm.
SGA Polymers, *Bio-Based Acrylic Acid Technology*, sgapolymers.com (online), [accessed Mar. 9, 2017], 1 page, URL: www.sgapolymers.com.

\* cited by examiner

US 10,160,838 B2

CROSSLINKING MATERIALS FROM BIORENEWABLE ACONITIC ACID

BACKGROUND

Polydimethylsiloxane (PDMS) is among the most widely used silicon-based polymers, and the most widely used organic silicon-based polymer. PDMS materials have a wide range of applications including contact lenses, medical devices, soft lithography processes, shampoos, caulking, and lubricants (among other alternatives). One reason for the wide-ranging applications for PDMS materials is the variety of ways in which the properties of PDMS may be controlled through polymer crosslinking. By employing PDMS and small organic molecules with different organic functional groups, many possibilities exist for different PDMS materials to be crosslinked in different ways.

SUMMARY

According to an embodiment, a process of forming a bio-derived crosslinking material from biorenewable aconitic acid is disclosed. The process includes initiating a chemical reaction to form a bio-derived crosslinking material that includes multiple functional groups. The chemical reaction includes converting each carboxylic acid group of a biorenewable aconitic acid molecule to one of the multiple functional groups.

According to another embodiment, a process of forming a crosslinked polymeric material is disclosed. The process includes utilizing a material derived from a biorenewable aconitic acid molecule as a bio-derived crosslinking material to form the crosslinked polymeric material.

According to another embodiment, a crosslinked polydimethylsiloxane (PDMS) material is disclosed. The crosslinked PDMS material is formed by a process that comprises chemically reacting a functionalized PDMS material with a bio-derived crosslinking material that is derived from a biorenewable aconitic acid molecule.

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes crosslinkers derived from the biorenewable molecule aconitic acid (cis-aconitic acid and/or trans-aconitic acid) and methods of forming bio-derived crosslinkers from the biorenewable molecule aconitic acid. The biorenewable molecule aconitic acid is an organic acid that may be derived from sugarcane or citric acid. The multiple carboxyl groups make the biorenewable molecule aconitic acid a suitable cross-linking agent. In the present disclosure, prior to cross-linking, aconitic acid may be reacted with other bio-derived organic molecules, reduced, or reduced and then reacted with other bio-derived organic molecules to synthesize different cross-linkable molecules with a variety of functional groups (e.g., for binding into a variety of polymer systems). Utilizing derivatives of biorenewable aconitic acid as crosslinking materials may increase the biorenewable content of a crosslinked polymeric material, such as a crosslinked polydimethylsiloxane (PDMS) material, for use in various applications.

The bio-derived crosslinking materials of the present disclosure may be applied to PDMS (or other polymers) for different applications. Examples of alternative polymers include polyethylene (PE), polypropylene (PP), polycarbonate (PC), polyurethane (PU), or acrylics, among other alternatives. In some cases, curing may be performed during processing of a desired material, resulting in a completely crosslinked polymer. In other cases, the crosslinkers may be mixed with PDMS but left in a partial or un-crosslinked state that can be left to crosslink upon addition to the PDMS for a particular desired application (e.g., for a caulking or coating application, among other alternatives).

FIGS. 1A, 1B, 2A, 2B, 3A, 3B, 4A, and 4B illustrate examples of cross-linkable molecules that may be formed from the biorenewable molecule aconitic acid. FIGS. 1A, 2A, 3A, and 4A illustrate that the cis-aconitic acid isomer may be modified with one of a variety of functional groups that are used to cross-link or cure polymers, such as PDMS (among other alternatives). FIGS. 1B, 2B, 3B, and 4B illustrate that the trans-aconitic acid isomer may modified with one of a variety of functional groups that are used to cross-link or cure polymers, such as PDMS (among other alternatives).

Figure 5A:
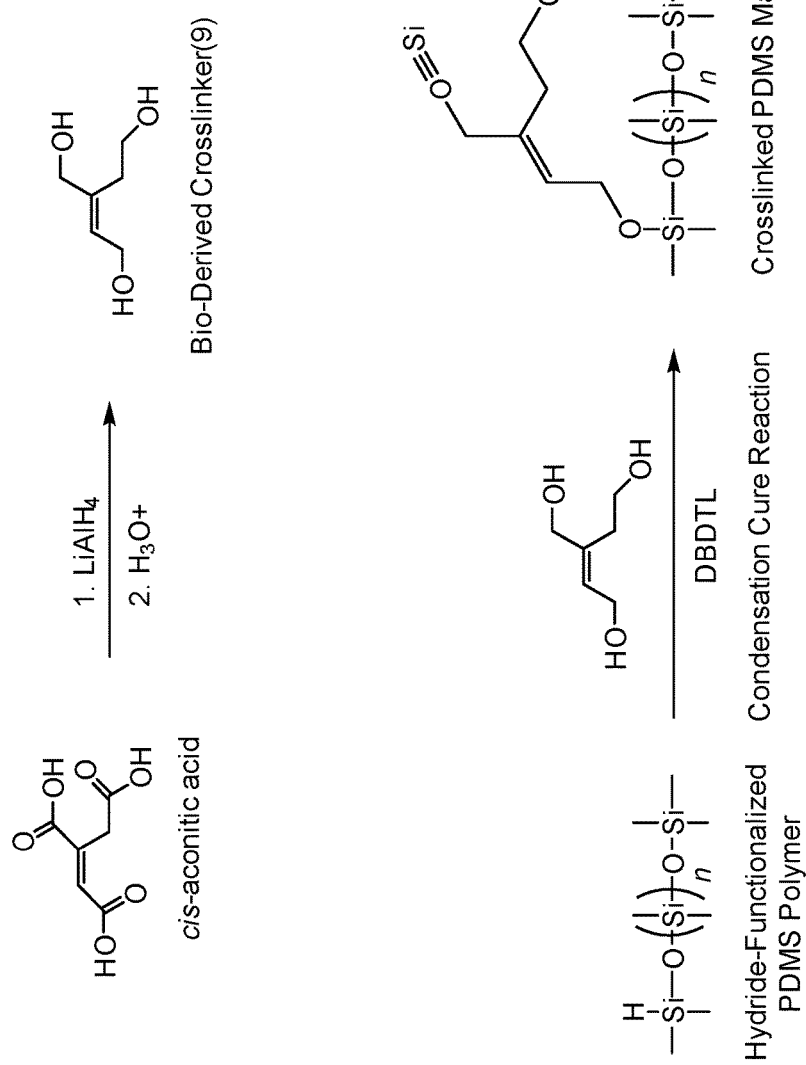
FIG. 5A is a chemical reaction diagram illustrating a process of forming a crosslinked PDMS material using a bio-derived crosslinking material having multiple hydroxyl groups that is formed via reduction of a biorenewable cis-aconitic acid molecule, according to one embodiment.
Figure 5B:
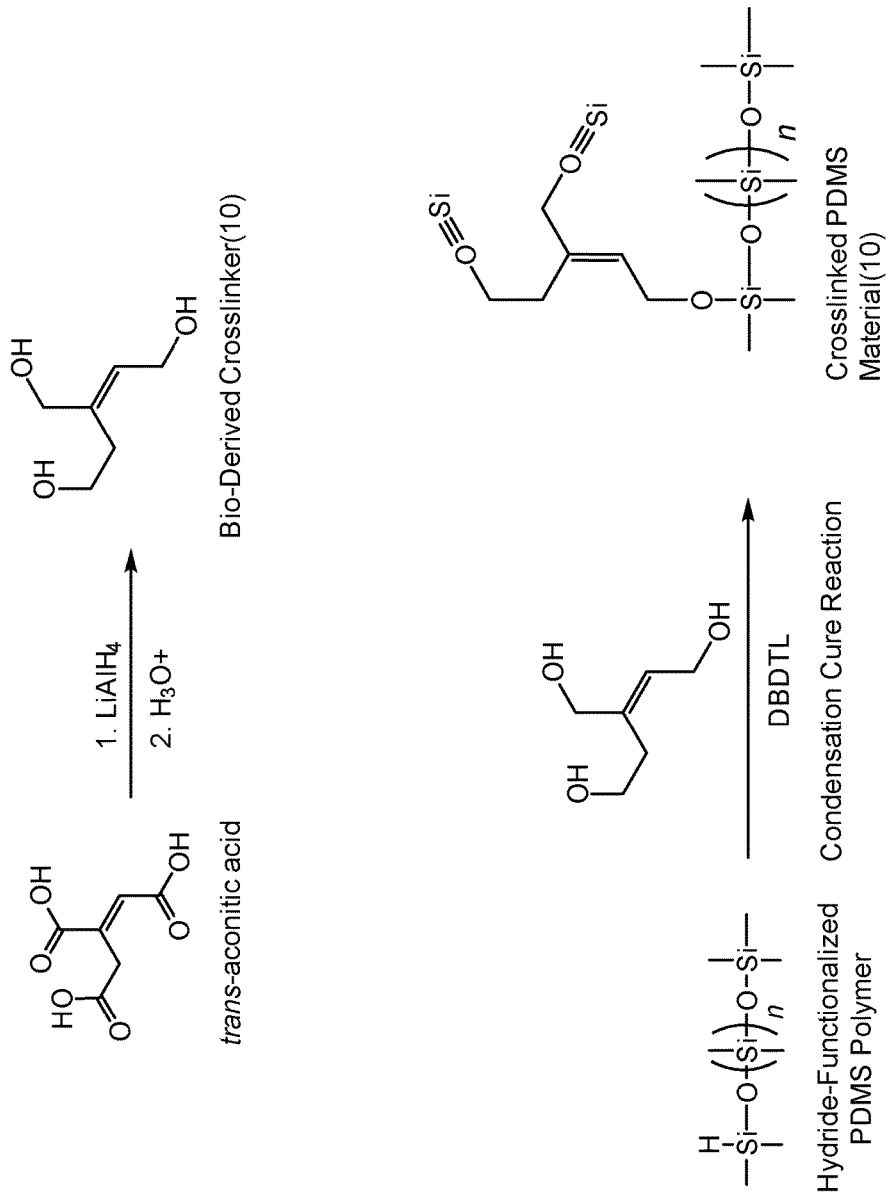
FIG. 5B is a chemical reaction diagram illustrating a process of forming a crosslinked PDMS material using a bio-derived crosslinking material having multiple hydroxyl groups that is formed via reduction of a biorenewable trans-aconitic acid molecule, according to one embodiment.

FIGS. 5A and 5B illustrate that the biorenewable molecule aconitic acid may be reduced to a tri-alcohol and used on its own as a cross-linker, with FIG. 5A illustrating the reduction of the cis-aconitic acid isomer and FIG. 5B illustrating the reduction of the trans-aconitic acid isomer.

FIGS. 6A, 6B, 7A, 7B, 8A, 8B, 9A, 9B, 10A, and 10B illustrate examples of cross-linkable molecules that may be formed from the reduced aconitic acid molecules depicted in FIGS. 5A and 5B. FIGS. 6A, 7A, 8A, 9A, and 10A illustrate that the reduced aconitic acid molecule formed from the cis-aconitic acid isomer (as depicted in FIG. 5A) may modified with one of a variety of functional groups that are used to cross-link or cure polymers, such as PDMS (among other alternatives). FIGS. 6B, 7B, 8B, 9B, and 10B illustrate that the reduced aconitic acid molecule formed from the trans-aconitic acid isomer (as depicted in FIG. 5B) may modified with one of a variety of functional groups that are used to cross-link or cure polymers, such as PDMS (among other alternatives).

Figure 1A:
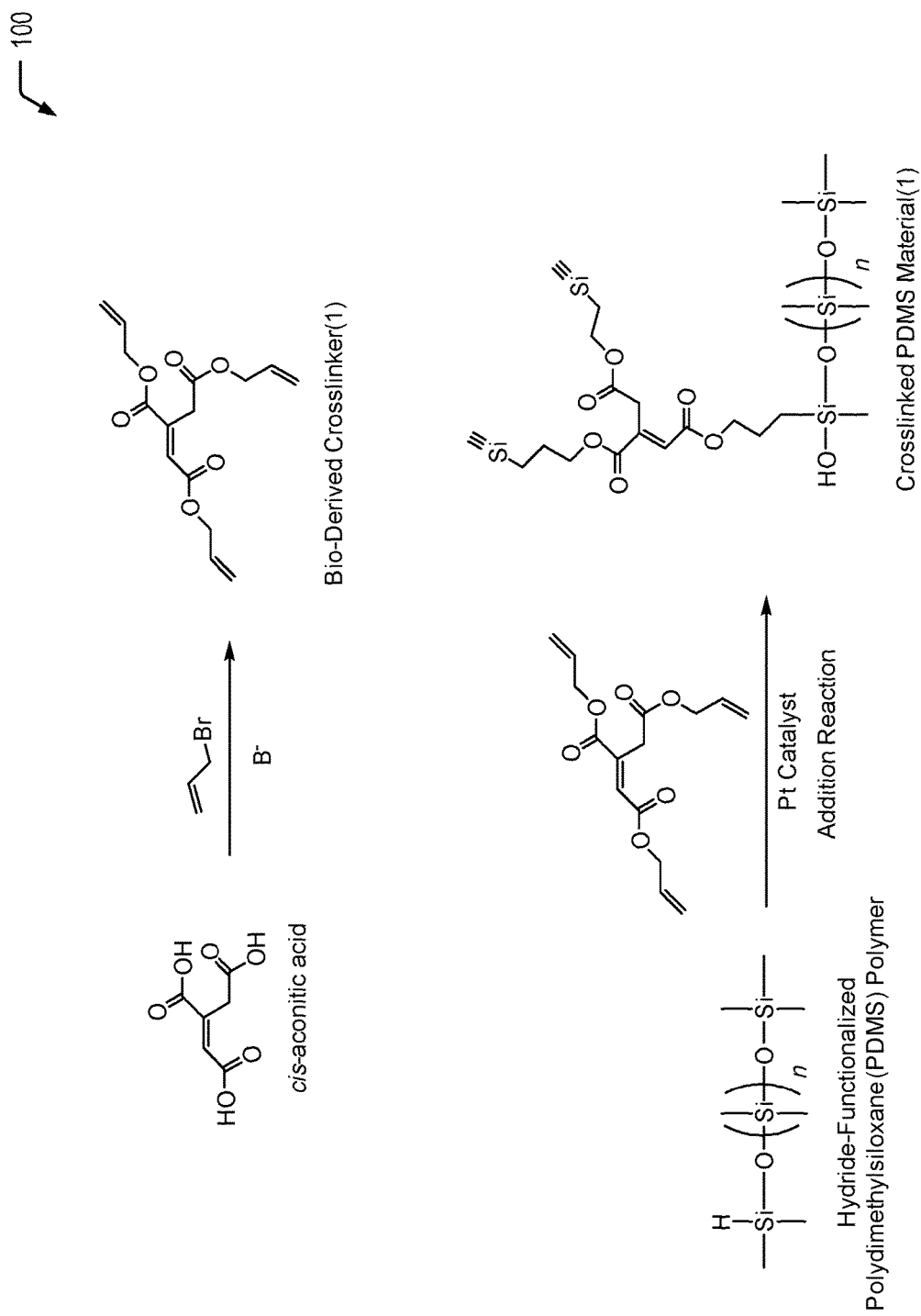
FIG. 1A is a chemical reaction diagram illustrating a process of forming a crosslinked PDMS material using a bio-derived crosslinking material having multiple vinyl groups that is formed from a biorenewable cis-aconitic acid molecule, according to one embodiment.

Referring to FIG. 1A, a chemical reaction diagram 100 illustrates a particular embodiment of a process of utilizing the biorenewable cis-aconitic acid isomer to form a first bio-derived crosslinking material (identified as "Bio-Derived Crosslinker(1)" in FIG. 1A) that includes multiple vinyl groups. FIG. 1A further illustrates that the first bio-derived crosslinking material may be utilized to form a crosslinked polymeric material (e.g., a crosslinked PDMS material), according to one embodiment.

The first chemical reaction depicted at the top of FIG. 1A illustrates that the cis-aconitic acid molecule may be reacted with allyl bromide via a substitution reaction to form a crosslinker with multiple vinyl groups. In some cases, the allyl bromide may be synthesized in one step from biorenewable allyl alcohol.

As a prophetic example, cis-aconitic acid may be added to a suspension or solution of a base (e.g., potassium carbonate) in an organic solvent, such as ethanol, at 0° C. The reaction mixture may be stirred for 10 minutes before adding allyl bromide (4 equiv.), dropwise. The reaction mixture may be stirred for approximately 7 days and then deionized water is added to generate an aqueous phase. The aqueous and organic layers may then be separated. The aqueous layer may be extracted with a suitable solvent and rinsed with brine. The organic layer may be dried over magnesium sulfate ($MgSO_4$) and the solvent may be removed in vacuo. The residue is purified by distillation or column chromatography.

The second chemical reaction depicted at the bottom of FIG. 1A illustrates that the bio-derived crosslinking material having multiple vinyl groups may be utilized to form a crosslinked polymeric material (identified as "Crosslinked PDMS Material(1)" in FIG. 1A). FIG. 1A illustrates a particular embodiment of an addition reaction that utilizes a platinum (Pt) catalyst. As a prophetic example, a hydride-functionalized siloxane may be blended with the first bio-derived crosslinking material having multiple vinyl groups (1-20% w/w) and Pt catalyst, such as Speier's catalyst ($H_2PtCl_6$) or Karstedt's catalyst ($C_{24}H_{54}O_3Pt_2Si_6$), and are then mixed. An addition cure reaction via hydrosilation may be performed on the mixture.

FIG. 1A depicts an example in which all three vinyl groups of the bio-derived crosslinking material react in the addition reaction. Depending on the reaction conditions, all three vinyl groups may be used to crosslink the PDMS polymer or less than three vinyl groups may be used for crosslinking. To illustrate, by controlling the reaction conditions, catalyst type (other tin or platinum catalyst may be used), catalyst loading, and stoichiometry, a fraction of the vinyl groups can be used for PDMS crosslinking. The ability to control the number of vinyl groups that react may enable better control of the mechanical properties of the final polymer.

Thus, FIG. 1A illustrates an example of a process of forming a bio-derived crosslinking material having multiple vinyl groups from the biorenewable cis-aconitic acid isomer and utilizing the bio-derived crosslinking material to form a crosslinked polymeric material via an addition reaction. The bio-derived crosslinking material of FIG. 1A may be used to increase the biorenewable content of a resulting crosslinked polymeric material (e.g., a crosslinked PDMS material).

Figure 1B:
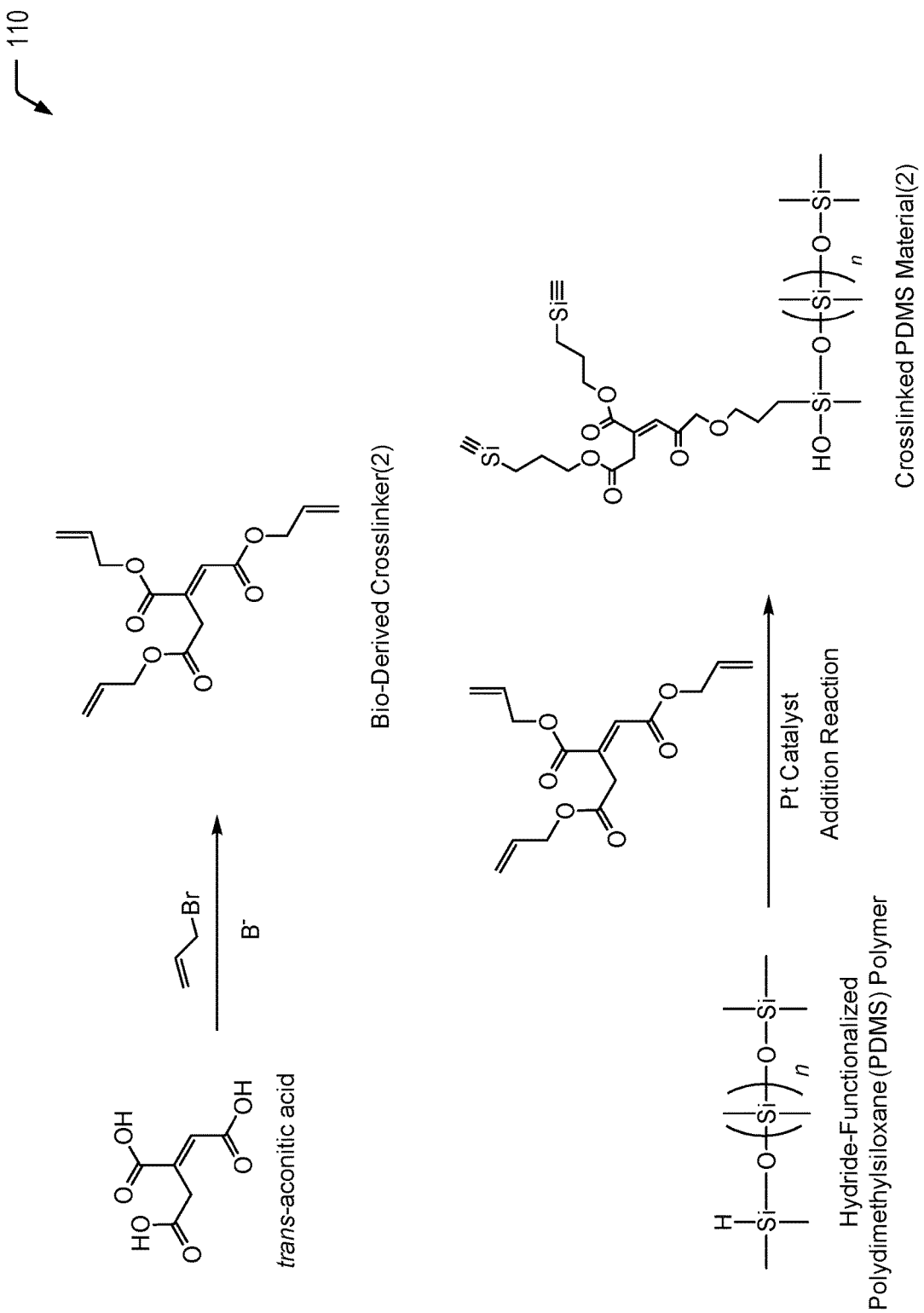
FIG. 1B is a chemical reaction diagram illustrating a process of forming a crosslinked PDMS material using a bio-derived crosslinking material having multiple vinyl groups that is formed from a biorenewable trans-aconitic acid molecule, according to one embodiment.

Referring to FIG. 1B, a chemical reaction diagram 110 illustrates a particular embodiment of a process of utilizing the biorenewable trans-aconitic acid isomer to form a second bio-derived crosslinking material (identified as "Bio-Derived Crosslinker(2)" in FIG. 1B) that includes multiple vinyl groups. FIG. 1B further illustrates that the second bio-derived crosslinking material may be utilized to form a crosslinked polymeric material (e.g., a crosslinked PDMS material), according to one embodiment.

The first chemical reaction depicted at the top of FIG. 1B illustrates that the trans-aconitic acid molecule may be reacted with allyl bromide via a substitution reaction to form a crosslinker with multiple vinyl groups. In some cases, the allyl bromide may be synthesized in one step from biorenewable allyl alcohol. The bio-derived crosslinking material depicted in FIG. 1B may be formed according to a process that is similar to the process previously described herein with respect to the bio-derived crosslinking material of FIG. 1A.

The second chemical reaction depicted at the bottom of FIG. 1B illustrates that the bio-derived crosslinking material having multiple vinyl groups may be utilized to form a crosslinked polymeric material (identified as "Crosslinked PDMS Material(2)" in FIG. 1B). The crosslinked polymeric material depicted in FIG. 1B may be formed according to a process that is similar to the process previously described herein with respect to the crosslinked polymeric material of FIG. 1A.

FIG. 1B depicts an example in which all three vinyl groups of the bio-derived crosslinking material react in the addition reaction. Depending on the reaction conditions, all three vinyl groups may be used to crosslink the PDMS polymer or less than three vinyl groups may be used for crosslinking. To illustrate, by controlling the reaction conditions, catalyst type (other tin or platinum catalyst may be used), catalyst loading, and stoichiometry, a fraction of the vinyl groups can be used for PDMS crosslinking. The ability to control the number of vinyl groups that react may enable better control of the mechanical properties of the final polymer.

Thus, FIG. 1B illustrates an example of a process of forming a bio-derived crosslinking material having multiple vinyl groups from the biorenewable trans-aconitic acid isomer and utilizing the bio-derived crosslinking material to form a crosslinked polymeric material via an addition reaction. The bio-derived crosslinking material of FIG. 1B may be used to increase the biorenewable content of a resulting crosslinked polymeric material (e.g., a crosslinked PDMS material).

Figure 2A:
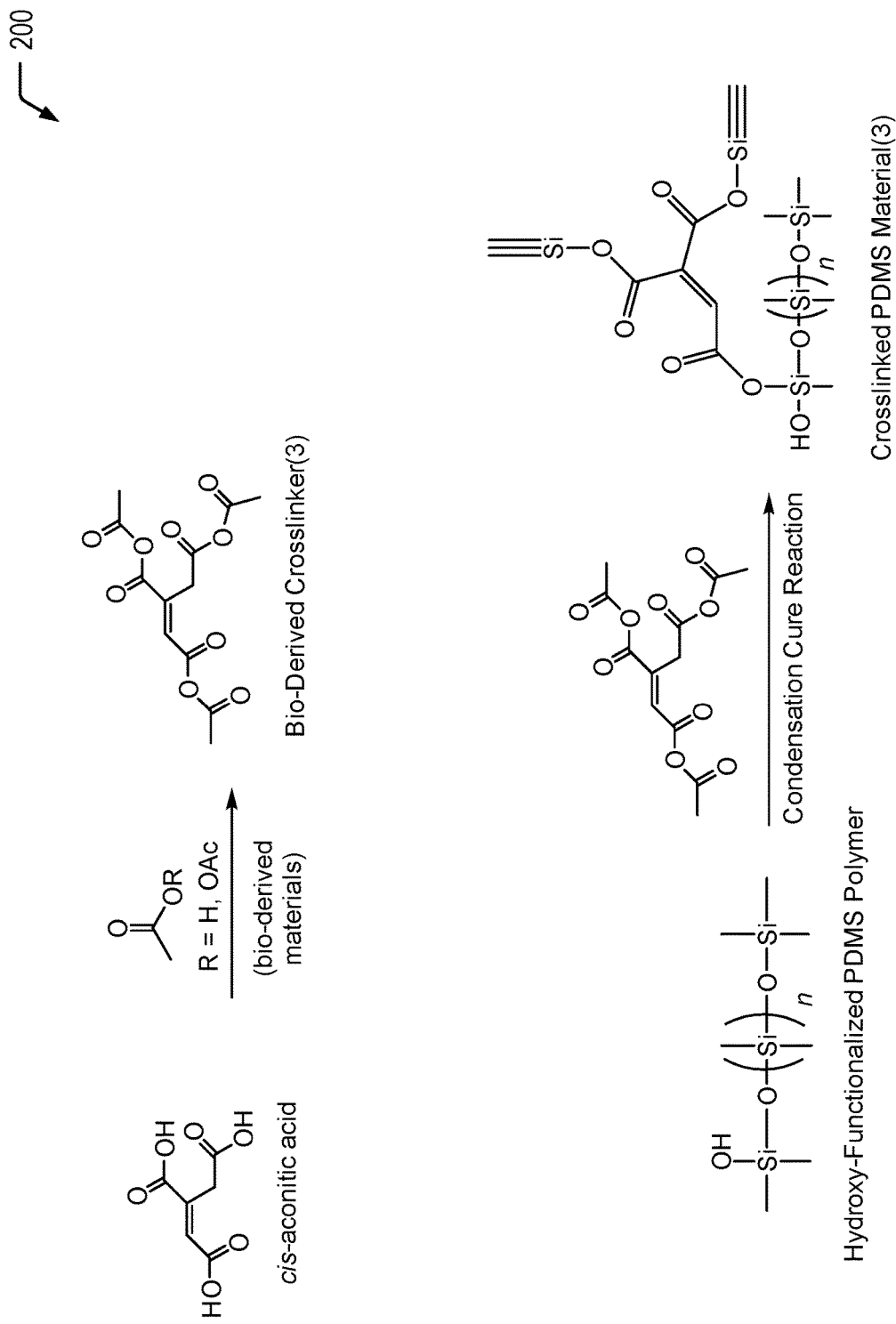
FIG. 2A is a chemical reaction diagram illustrating a process of forming a crosslinked PDMS material using a bio-derived crosslinking material having multiple acetate groups that is formed from a biorenewable cis-aconitic acid molecule, according to one embodiment.

Referring to FIG. 2A, a chemical reaction diagram 200 illustrates a particular embodiment of a process of utilizing the biorenewable cis-aconitic acid isomer to form a third bio-derived crosslinking material (identified as "Bio-Derived Crosslinker(3)" in FIG. 2A) that includes multiple acetate groups. FIG. 2A further illustrates that the bio-derived crosslinking material may be utilized to form a crosslinked polymeric material (e.g., a crosslinked PDMS material), according to one embodiment.

The first chemical reaction depicted at the top of FIG. 2A illustrates that the cis-aconitic acid molecule may be reacted with acetic acid or acetic anhydride via an acylation reaction to form a crosslinker that includes multiple acetate groups. Alternatively, acetyl chloride may be formed from the acetic acid or purchased from a commercial source, and may be used in place of acetic acid along with an amine which may be pyridine or triethylamine. The acetic acid may be obtained from renewable sources, and acetic anhydride can be synthesized from acetic acid.

As a prophetic example, cis-aconitic acid (1 equiv.), acetic acid (4.5-5.0 equiv.), catalytic p-toluenesulfonic acid (or other catalysts such as sulfonic acids, sulfuric acid, phosphoric acid, hydrogen sulfates, dihydrogen phosphates, phosphonic acid esters, or dialkyl tin dioxides) or a Lewis base such as dimethylaminopyridine (DMAP), and a suitable amount of toluene (or other water-azeotrope forming solvents) may be added to a reaction vessel and heated under azeotropic distillation conditions (e.g., refluxing using a Dean-Stark apparatus) until water is no longer removed from the reaction. The mixture may be cooled to room temperature, and the organic layer may be separated, rinsed with water, dried, and purified.

The second chemical reaction depicted at the bottom of FIG. 2A illustrates that the bio-derived crosslinking material having multiple acetate groups may be utilized to form a crosslinked polymeric material via a condensation cure reaction. As a prophetic example, a hydroxy-functionalized siloxane may be mixed with the second bio-derived crosslinker having multiple acetate groups (1-50% w/w) and blended with exclusion of moisture. The blended mixture may be stored under moisture-free conditions. The blended mixture may be applied to surfaces and materials and allowed to cure under atmospheric conditions.

FIG. 2A depicts an example in which all three acetate groups of the bio-derived crosslinking material react in the condensation cure reaction. Depending on the reaction conditions, all three acetate groups may be used to crosslink the PDMS polymer or less than three acetate groups may be used for crosslinking. The ability to control the number of acetate groups that react may enable better control of the mechanical properties of the final polymer.

Thus, FIG. 2A illustrates an example of a process of forming a bio-derived crosslinking material having multiple acetate groups from the biorenewable cis-aconitic acid isomer and utilizing the bio-derived crosslinking material to form a crosslinked polymeric material via a condensation cure reaction. The bio-derived crosslinking material of FIG. 2A may be used to increase the biorenewable content of a resulting crosslinked polymeric material (e.g., a crosslinked PDMS material).

Figure 2B:
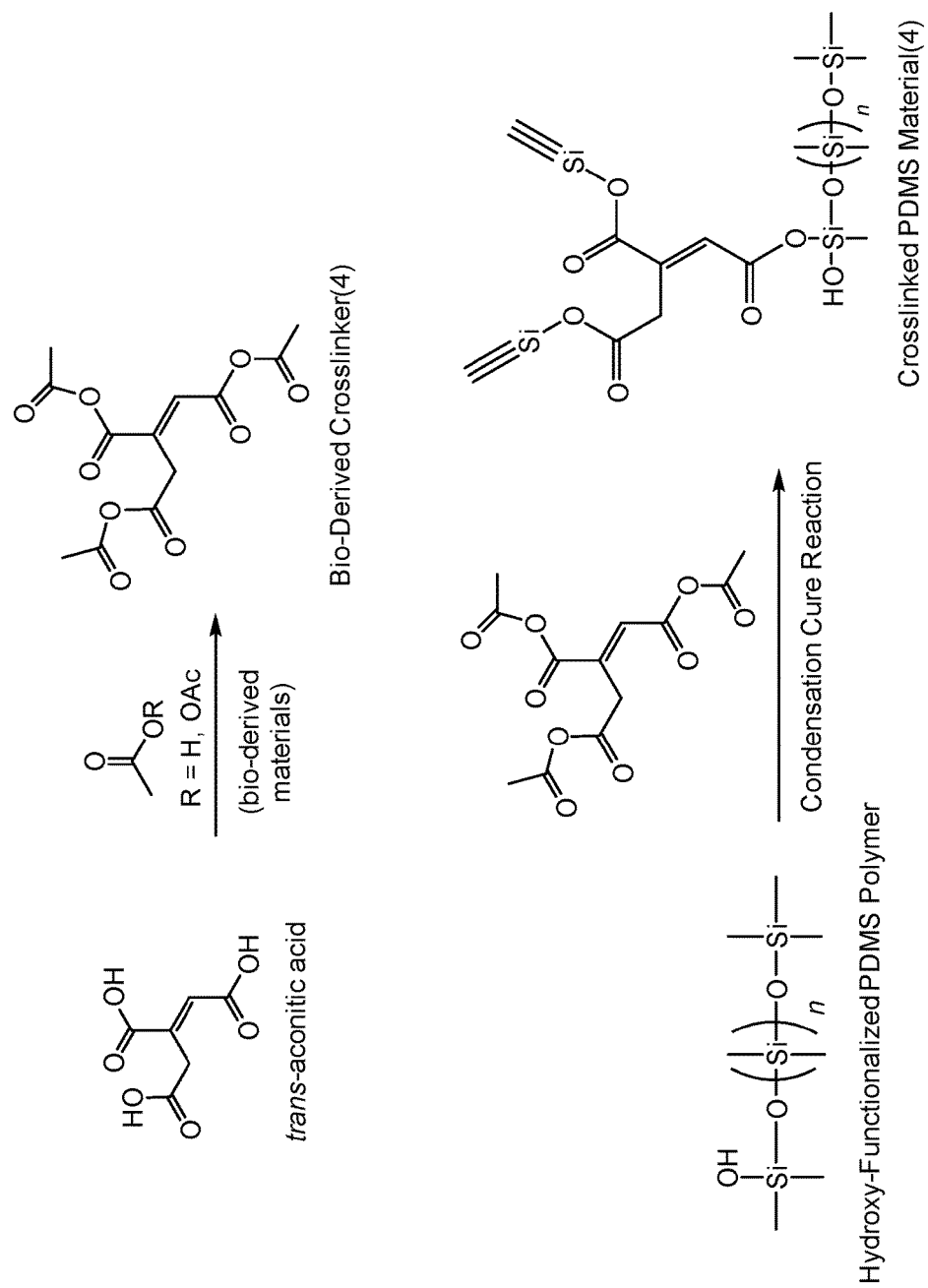
FIG. 2B is a chemical reaction diagram illustrating a process of forming a crosslinked PDMS material using a bio-derived crosslinking material having multiple acetate groups that is formed from a biorenewable trans-aconitic acid molecule, according to one embodiment.

Referring to FIG. 2B, a chemical reaction diagram 210 illustrates a particular embodiment of a process of utilizing the biorenewable trans-aconitic acid isomer to form a fourth bio-derived crosslinking material (identified as "Bio-Derived Crosslinker(4)" in FIG. 2B) that includes multiple acetate groups. FIG. 2B further illustrates that the bio-derived crosslinking material may be utilized to form a crosslinked polymeric material (e.g., a crosslinked PDMS material), according to one embodiment.

The first chemical reaction depicted at the top of FIG. 2B illustrates that the trans-aconitic acid molecule may be reacted with acetic acid or acetic anhydride via an acylation reaction to form a crosslinker that includes multiple acetate groups. Alternatively, acetyl chloride may be formed from the acetic acid or purchased from a commercial source, and may be used in place of acetic acid along with an amine which may be pyridine or triethylamine. The acetic acid may be obtained from renewable sources, and acetic anhydride can be synthesized from acetic acid. The bio-derived crosslinking material depicted in FIG. 2B may be formed according to a process that is similar to the process previously described herein with respect to the bio-derived crosslinking material of FIG. 2A.

The second chemical reaction depicted at the bottom of FIG. 2B illustrates that the bio-derived crosslinking material having multiple acetate groups may be utilized to form a crosslinked polymeric material via a condensation cure reaction. The crosslinked polymeric material depicted in FIG. 2B may be formed according to a process that is similar to the process previously described herein with respect to the crosslinked polymeric material of FIG. 2A.

FIG. 2B depicts an example in which all three acetate groups of the bio-derived crosslinking material react in the condensation cure reaction. Depending on the reaction conditions, all three acetate groups may be used to crosslink the PDMS polymer or less than three acetate groups may be used for crosslinking. The ability to control the number of acetate groups that react may enable better control of the mechanical properties of the final polymer.

Thus, FIG. 2B illustrates an example of a process of forming a bio-derived crosslinking material having multiple acetate groups from the biorenewable trans-aconitic acid isomer and utilizing the bio-derived crosslinking material to form a crosslinked polymeric material via a condensation cure reaction. The bio-derived crosslinking material of FIG. 2B may be used to increase the biorenewable content of a resulting crosslinked polymeric material (e.g., a crosslinked PDMS material).

Figure 3A:
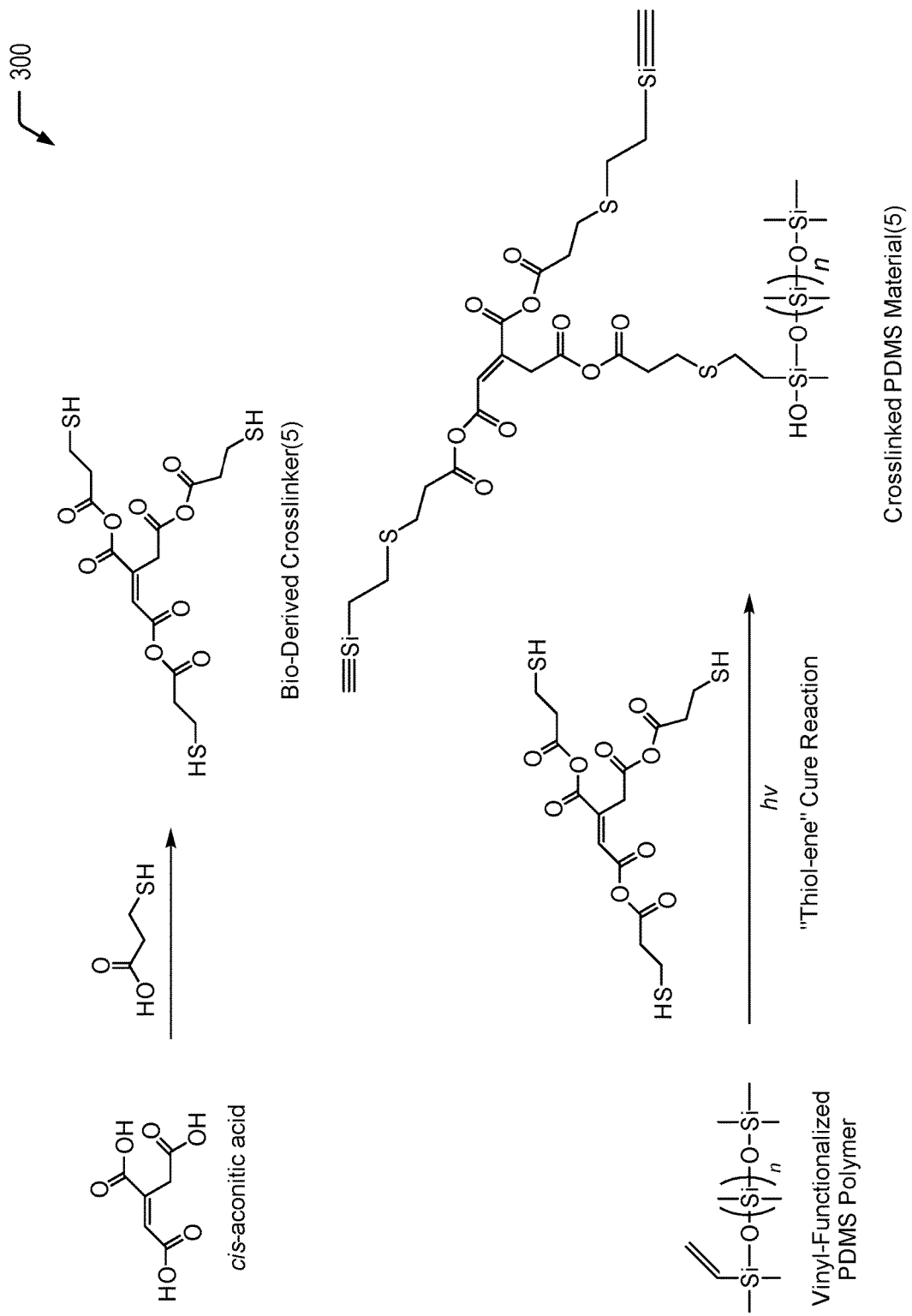
FIG. 3A is a chemical reaction diagram illustrating a process of forming a crosslinked PDMS material using a bio-derived crosslinking material having multiple thiol groups that is formed from a biorenewable cis-aconitic acid molecule, according to one embodiment.

Referring to FIG. 3A, a chemical reaction diagram 300 illustrates a particular embodiment of a process of utilizing the biorenewable cis-aconitic acid isomer to form a fifth bio-derived crosslinking material (identified as "Bio-Derived Crosslinker(5)" in FIG. 3A) that includes multiple thiol (or mercapto) groups. FIG. 3A further illustrates that the bio-derived crosslinking material may be utilized to form a crosslinked polymeric material (e.g., a crosslinked PDMS material), according to one embodiment.

The first chemical reaction depicted at the top of FIG. 3A illustrates that the cis-aconitic acid molecule may be reacted with ethyl mercaptoacetic acid via a condensation reaction (acid/base promoted) to synthesize a crosslinker with multiple thiol (or mercapato) groups. The ethyl mercaptoacetic acid may be synthesized from biorenewable acrylic acid via subsequent halogenation and substitution reactions.

As a prophetic example, cis-aconitic acid (1 equiv.), 3-mercaptopropionic acid (4.5-5.0 equiv.), catalytic p-toluenesulfonic acid (or other catalysts such as sulfonic acids, triflic acid, sulfuric acid, phosphoric acid, hydrogen sulfates, dihydrogen phosphates, phosphonic acid esters, or dialkyl tin dioxides) or a Lewis base such as dimethylaminopyridine (DMAP), 1,8-Diazabicyclo[5.4.0]undec-7-ene (DBU), or triphenylphosphine, and a suitable amount of toluene (or other water-azeotrope forming solvents) may be added to a reaction vessel and heated under azeotropic distillation conditions (e.g., refluxing using a Dean-Stark apparatus) until water is no longer removed from the reaction. The mixture may be cooled to room temperature, and the organic layer may be separated, rinsed with water, dried, and purified.

The second chemical reaction depicted at the bottom of FIG. 3A illustrates that the bio-derived crosslinking material having multiple thiol groups may be utilized to form a crosslinked polymeric material via a thiol-ene cure reaction. As a prophetic example, the bio-derived crosslinking material having multiple thiol groups (2-6% w/w) may be mixed with a vinyl-functionalized siloxane. The mixture may include a radical initiator, such as Micheler's ketone, an alpha-amino-ketone, an alpha-hydroxy-ketone, a benzyldimethyl ketal, or benzophenone (among other alternatives). The mixture may be applied to molds or coated onto a substrate and cured under UV light at a time and temperature suitable to the included radical initiators that are appropriate for the desired applications.

FIG. 3A depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. The ability to control the number of thiol groups that react may enable better control of the mechanical properties of the final polymer.

Thus, FIG. 3A illustrates an example of a process of forming a bio-derived crosslinking material having multiple thiol (or mercapto) groups from the biorenewable cis-aconitic acid isomer and utilizing the bio-derived crosslinking material to form a crosslinked polymeric material via a thiol-ene cure reaction. The bio-derived crosslinking material of FIG. 3A may be used to increase the biorenewable content of a resulting crosslinked polymeric material (e.g., a crosslinked PDMS material).

Figure 3B:
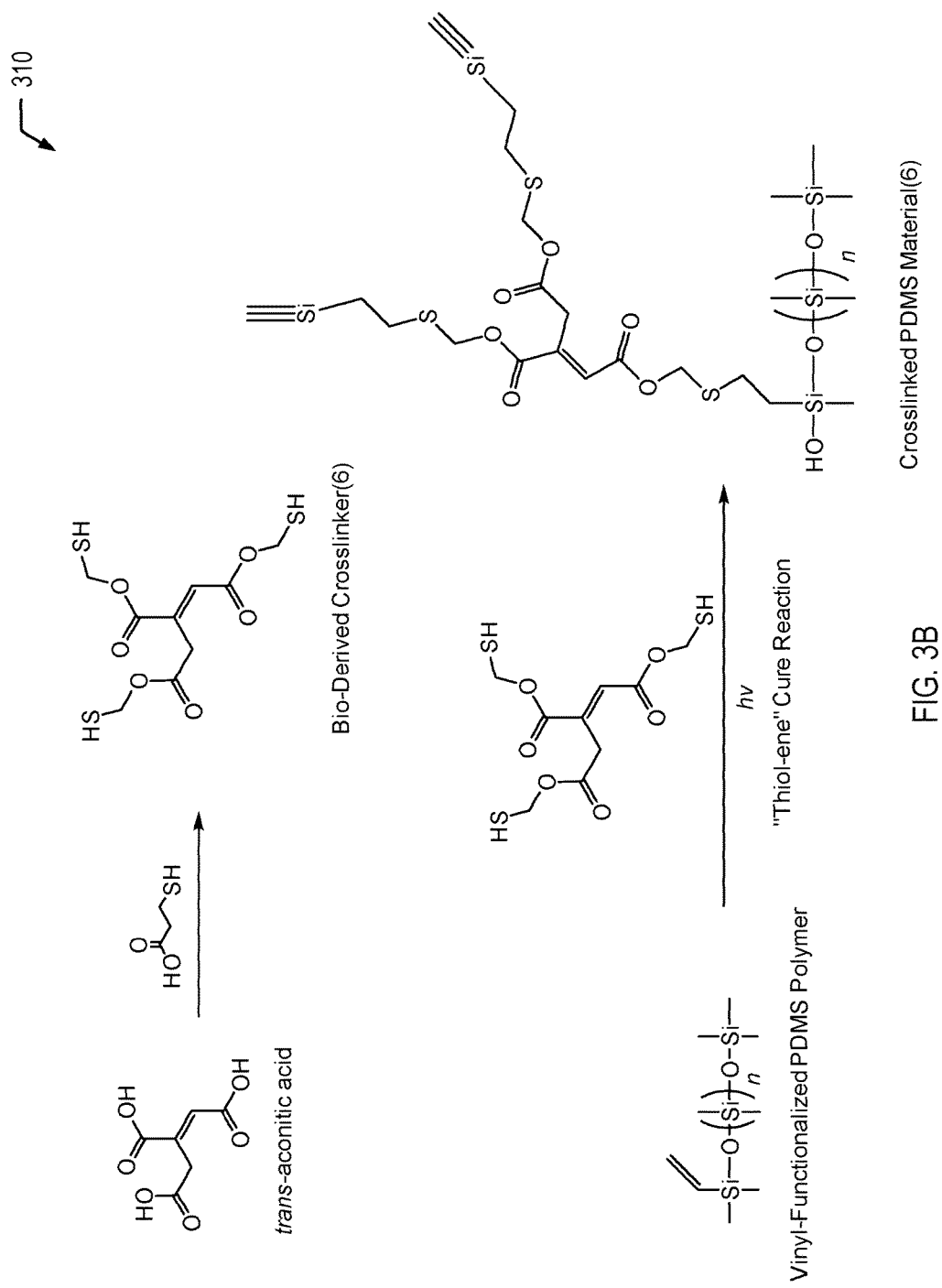
FIG. 3B is a chemical reaction diagram illustrating a process of forming a crosslinked PDMS material using a bio-derived crosslinking material having multiple thiol groups that is formed from a biorenewable trans-aconitic acid molecule, according to one embodiment.

Referring to FIG. 3B, a chemical reaction diagram 310 illustrates a particular embodiment of a process of utilizing the biorenewable trans-aconitic acid isomer to form a sixth bio-derived crosslinking material (identified as "Bio-Derived Crosslinker(6)" in FIG. 3B) that includes multiple thiol (or mercapto) groups. FIG. 3B further illustrates that the bio-derived crosslinking material may be utilized to form a crosslinked polymeric material (e.g., a crosslinked PDMS material), according to one embodiment.

The first chemical reaction depicted at the top of FIG. 3B illustrates that the trans-aconitic acid molecule may be reacted with ethyl mercaptoacetic acid via a condensation reaction (acid/base promoted) to synthesize a crosslinker with multiple thiol (or mercapato) groups. The ethyl mercaptoacetic acid may be synthesized from biorenewable acrylic acid via subsequent halogenation and substitution reactions. The bio-derived crosslinking material depicted in FIG. 3B may be formed according to a process that is similar to the process previously described herein with respect to the bio-derived crosslinking material of FIG. 3A.

The second chemical reaction depicted at the bottom of FIG. 3B illustrates that the bio-derived crosslinking material having multiple thiol groups may be utilized to form a crosslinked polymeric material via a thiol-ene cure reaction. The crosslinked polymeric material depicted in FIG. 3B may be formed according to a process that is similar to the process previously described herein with respect to the crosslinked polymeric material of FIG. 3A.

FIG. 3B depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. The ability to control the number of thiol groups that react may enable better control of the mechanical properties of the final polymer.

Thus, FIG. 3B illustrates an example of a process of forming a bio-derived crosslinking material having multiple thiol (or mercapto) groups from the biorenewable trans-aconitic acid isomer and utilizing the bio-derived crosslinking material to form a crosslinked polymeric material via a thiol-ene cure reaction. The bio-derived crosslinking material of FIG. 3B may be used to increase the biorenewable content of a resulting crosslinked polymeric material (e.g., a crosslinked PDMS material).

Figure 4A:
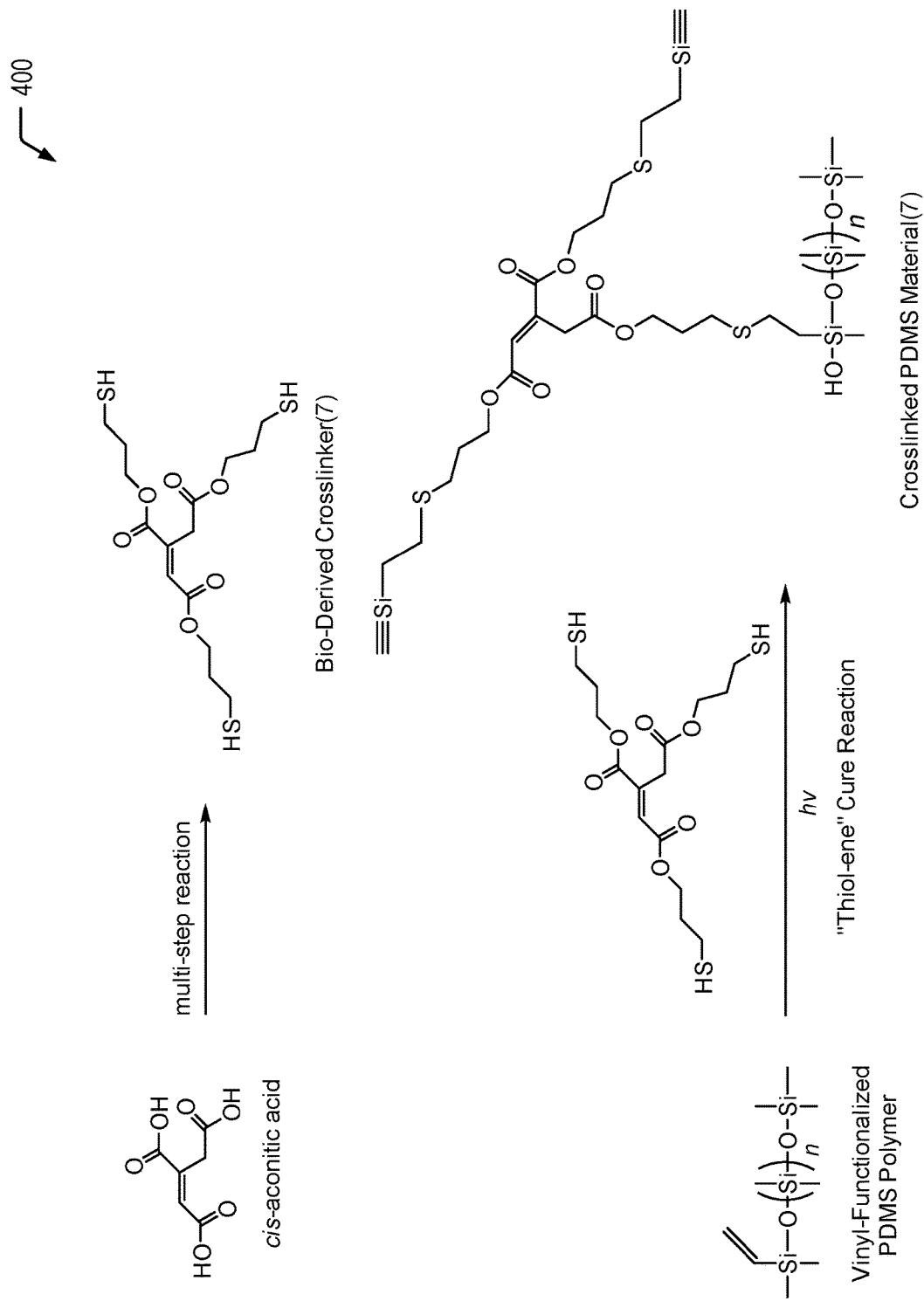
FIG. 4A is a chemical reaction diagram illustrating a process of forming a crosslinked PDMS material using a bio-derived crosslinking material having multiple thiol groups that is formed from a biorenewable cis-aconitic acid molecule, according to one embodiment.

Referring to FIG. 4A, a chemical reaction diagram 400 illustrates a particular embodiment of a process of utilizing the biorenewable cis-aconitic acid isomer to form a seventh bio-derived crosslinking material (identified as "Bio-Derived Crosslinker(7)" in FIG. 4A) that includes multiple thiol (or mercapto) groups. FIG. 4A further illustrates that the bio-derived crosslinking material may be utilized to form a crosslinked polymeric material (e.g., a crosslinked PDMS material), according to one embodiment.

The first chemical reaction depicted at the top of FIG. 4A illustrates that the cis-aconitic acid molecule may be utilized to form a crosslinker with multiple thiol (or mercapto) groups via a multiple step reaction that includes the use of an acetate protected thiol bromopropane (commercially available) and substitution chemistry, then removing the protecting group. As a prophetic example, cis-aconitic acid may be added to a suspension or solution of a base (e.g., sodium hydride) in an organic solvent, such as tetrahydrofuran (THF), diethyl ether, or N,N-dimethylformamide (DMF) at 0° C. The reaction mixture may be stirred for 30 minutes before adding S-(3-bromopropyl)ethanethioic acid ester (>3 equiv.), dropwise. The reaction mixture may be stirred for approximately 3 hours, and then neutralized by hydrochloric (HCl) acid. The aqueous and organic layers may then be separated. The aqueous layer may be extracted with diethyl ether, and rinsed with brine. The organic layer may be dried over magnesium sulfate ($MgSO_4$), and the solvent may be removed in vacuo. The residue may be purified by distillation or column chromatography. The resultant product may be dissolved in DCM at 0° C. and an acid such as trifluoroacetic acid may be added, dropwise. The reaction may be stirred for 3 hours at room temperature, and poured into water. The aqueous and organic layers may then be separated. The aqueous layer may then be extracted with diethyl ether, and rinsed with brine. The organic layer may be dried over magnesium sulfate ($MgSO_4$), and the solvent may be removed in vacuo. The residue is purified by distillation or column chromatography.

The second chemical reaction depicted at the bottom of FIG. 4A illustrates that the bio-derived crosslinking material having multiple thiol groups may be utilized to form a crosslinked polymeric material via a thiol-ene cure reaction. As a prophetic example, the bio-derived crosslinking material having multiple thiol groups (2-6% w/w) may be mixed with a vinyl-functionalized siloxane. The mixture may include a radical initiator, such as Micheler's ketone, an alpha-amino-ketone, an alpha-hydroxy-ketone, a benzyldimethyl ketal, or benzophenone (among other alternatives). The mixture may be applied to molds or coated onto a substrate and cured under UV light at a time and temperature suitable to the included radical initiators that are appropriate for the desired applications.

FIG. 4A depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. The ability to control the number of thiol groups that react may enable better control of the mechanical properties of the final polymer.

Thus, FIG. 4A illustrates an example of a process of forming a bio-derived crosslinking material having multiple thiol (or mercapto) groups from the biorenewable cis-aconitic acid isomer and utilizing the bio-derived crosslinking material to form a crosslinked polymeric material via a thiol-ene cure reaction. The bio-derived crosslinking material of FIG. 4A may be used to increase the biorenewable content of a resulting crosslinked polymeric material (e.g., a crosslinked PDMS material).

Figure 4B:
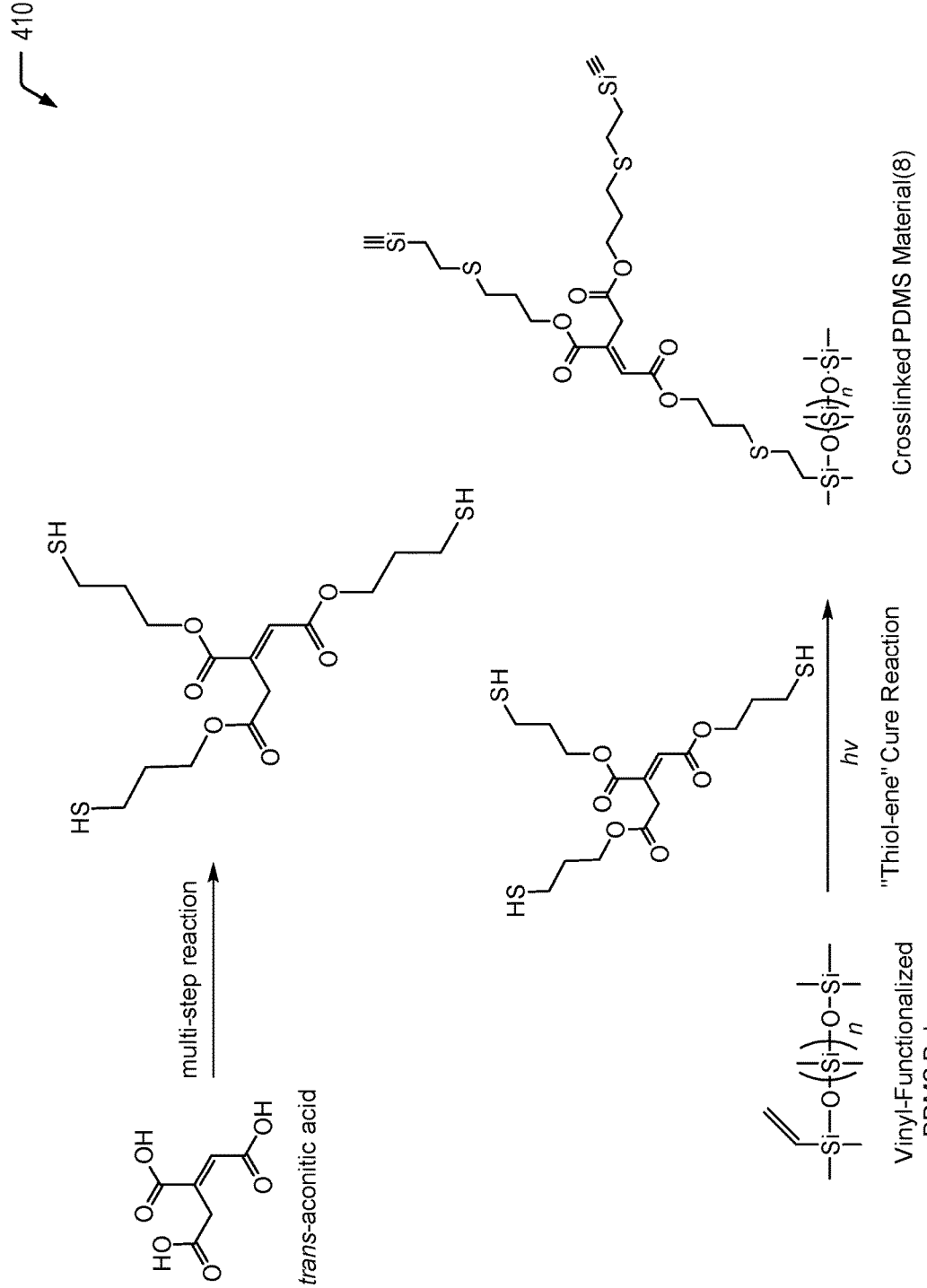
FIG. 4B is a chemical reaction diagram illustrating a process of forming a crosslinked PDMS material using a bio-derived crosslinking material having multiple thiol groups that is formed from a biorenewable trans-aconitic acid molecule, according to one embodiment.

Referring to FIG. 4B, a chemical reaction diagram 410 illustrates a particular embodiment of a process of utilizing the biorenewable trans-aconitic acid isomer to form an eighth bio-derived crosslinking material (identified as "Bio-Derived Crosslinker(8)" in FIG. 4B) that includes multiple thiol (or mercapto) groups. FIG. 4B further illustrates that the bio-derived crosslinking material may be utilized to form a crosslinked polymeric material (e.g., a crosslinked PDMS material), according to one embodiment.

The first chemical reaction depicted at the top of FIG. 4B illustrates that the trans-aconitic acid molecule may be utilized to form a crosslinker with multiple thiol (or mercapto) groups via a multiple step reaction that includes the use of an acetate protected thiol bromopropane (commercially available) and substitution chemistry, then removing the protecting group. The bio-derived crosslinking material depicted in FIG. 4B may be formed according to a process that is similar to the process previously described herein with respect to the bio-derived crosslinking material of FIG. 4A.

The second chemical reaction depicted at the bottom of FIG. 4B illustrates that the bio-derived crosslinking material having multiple thiol groups may be utilized to form a crosslinked polymeric material via a thiol-ene cure reaction. The crosslinked polymeric material depicted in FIG. 4B may be formed according to a process that is similar to the process previously described herein with respect to the crosslinked polymeric material of FIG. 4A.

FIG. 4B depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. The ability to control the number of thiol groups that react may enable better control of the mechanical properties of the final polymer.

Thus, FIG. 4B illustrates an example of a process of forming a bio-derived crosslinking material having multiple thiol (or mercapto) groups from the biorenewable trans-aconitic acid isomer and utilizing the bio-derived crosslinking material to form a crosslinked polymeric material via a thiol-ene cure reaction. The bio-derived crosslinking material of FIG. 4B may be used to increase the biorenewable content of a resulting crosslinked polymeric material (e.g., a crosslinked PDMS material).

FIGS. 5A and 5B illustrate that the biorenewable molecule aconitic acid may be reduced to a tri-alcohol and used on its own as a cross-linker, with FIG. 5A illustrating the reduction of the cis-aconitic acid isomer and FIG. 5B illustrating the reduction of the trans-aconitic acid isomer. Alternatively, FIGS. 6A, 6B, 7A, 7B, 8A, 8B, 9A, 9B, 10A, and 10B illustrate that the reduced aconitic acid molecules of FIGS. 5A and 5B could be further modified with one of a variety of different functional groups that are used to cross-link or cure polymers, like PDMS.

Referring to FIG. 5A, a chemical reaction diagram 500 illustrates a particular embodiment of a process of reducing the biorenewable cis-aconitic acid isomer to a tri-alcohol. The reduced aconitic acid molecule represents a ninth example of a bio-derived crosslinking material (identified as "Bio-Derived Crosslinker(9)" in FIG. 5A) that includes multiple hydroxyl groups. FIG. 5A further illustrates that the reduced aconitic acid molecule may be utilized to form a crosslinked polymeric material (e.g., a crosslinked PDMS material), according to one embodiment.

The first chemical reaction depicted at the top of FIG. 5A illustrates that the cis-aconitic acid molecule may be reduced to a tri-alcohol, (E)-3-(hydroxymethyl)pent-2-ene-1,5-diol, by lithium aluminum hydride (LiAlH$_4$). As a prophetic example, for every mole of carboxylic acid, use 3-5 molar equivalents of LiAlH$_4$. Under inert atmosphere/dry conditions, the carboxylic acid solution may be added dropwise to a solution that includes LiAlH$_4$ suspended in a solvent, such as tetrahydrofuran (THF) at 0° C. An example workup may include, for every X grams of LiAlH$_4$, slowly adding X mL of water, X mL of 15-25 percent NaOH (aq) solution, 3X mL of water, then allowing to warm to room temperature and stirring for variable amounts of time. Separated, precipitated salts may be washed, and the combined organic layer and extractions are dried with magnesium sulfate, then filtered.

The second chemical reaction depicted at the bottom of FIG. 5A illustrates that the reduced aconitic acid molecule that includes three hydroxyl functional groups may be utilized to form a crosslinked polymeric material via a condensation cure reaction. FIG. 5 illustrates a particular embodiment of a condensation cure reaction that utilizes dibutyltin dilaurate (DBTDL) as a catalyst. FIG. 5A depicts an example in which all three hydroxyl groups of the reduced aconitic acid molecule react in the condensation cure reaction. Depending on the reaction conditions, all three hydroxyl groups may be used to crosslink the PDMS polymer or less than three hydroxyl groups may be used for crosslinking. To illustrate, by controlling the reaction conditions, catalyst type (other tin or platinum catalyst may be used), catalyst loading, and stoichiometry, a fraction of the hydroxyl groups (e.g., less than three hydroxyl groups per reduced aconitic acid molecule, on average) can be used for PDMS crosslinking. The ability to control the number of hydroxyl groups that react may enable better control of the mechanical properties of the final polymer.

As a prophetic example, a hydride-functionalized siloxane may be blended with the tri-alcohol formed via reduction of the cis-aconitic acid isomer (about 1-20% w/w) and catalyst (DBDTL in this case, 0.1%-2.0% w/w) and mixed. The mixture may be applied to molds or coated onto a substrate and cured for times and temperatures that are appropriate for the desired applications.

Thus, FIG. 5A illustrates an example of a process of reducing the biorenewable cis-aconitic acid isomer to a tri-alcohol, and utilizing the reduced aconitic acid molecule as a bio-derived crosslinking material to form a crosslinked polymeric material via a condensation cure reaction. The bio-derived crosslinking material of FIG. 5A may be used to increase the biorenewable content of a resulting crosslinked polymeric material (e.g., a crosslinked PDMS material).

Referring to FIG. 5B, a chemical reaction diagram 510 illustrates a particular embodiment of a process of reducing the biorenewable trans-aconitic acid isomer to a tri-alcohol. The reduced aconitic acid molecule represents a tenth example of a bio-derived crosslinking material (identified as "Bio-Derived Crosslinker(10)" in FIG. 5B) that includes multiple hydroxyl groups. FIG. 5B further illustrates that the reduced aconitic acid molecule may be utilized to form a crosslinked polymeric material (e.g., a crosslinked PDMS material), according to one embodiment.

The first chemical reaction depicted at the top of FIG. 5B illustrates that the trans-aconitic acid molecule may be reduced to a tri-alcohol, (Z)-3-(hydroxymethyl)pent-2-ene-1,5-diol, by lithium aluminum hydride. The tri-alcohol depicted in FIG. 5B may be formed from the trans-aconitic acid isomer according to a process that is similar to the process previously described herein with respect to the tri-alcohol of FIG. 5A.

The second chemical reaction depicted at the bottom of FIG. 5B illustrates that the reduced aconitic acid molecule that includes three hydroxyl functional groups may be utilized to form a crosslinked polymeric material via a condensation cure reaction. The crosslinked polymeric material depicted in FIG. 5B may be formed according to a process that is similar to the process previously described herein with respect to the crosslinked polymeric material of FIG. 5A.

FIG. 5B depicts an example in which all three hydroxyl groups of the reduced aconitic acid molecule react in the condensation cure reaction. Depending on the reaction conditions, all three hydroxyl groups may be used to crosslink the PDMS polymer or less than three hydroxyl groups may be used for crosslinking. To illustrate, by controlling the reaction conditions, catalyst type (other tin or platinum catalyst may be used), catalyst loading, and stoichiometry, a fraction of the hydroxyl groups (e.g., less than three hydroxyl groups per reduced aconitic acid molecule, on average) can be used for PDMS crosslinking. The ability to control the number of hydroxyl groups that react may enable better control of the mechanical properties of the final polymer.

Thus, FIG. 5B illustrates an example of a process of reducing the biorenewable trans-aconitic acid isomer to a tri-alcohol, and utilizing the reduced aconitic acid molecule as a bio-derived crosslinking material to form a crosslinked polymeric material via a condensation cure reaction. The bio-derived crosslinking material of FIG. 5B may be used to increase the biorenewable content of a resulting crosslinked polymeric material (e.g., a crosslinked PDMS material).

FIGS. 6A, 7A, 8A, 9A, and 10A illustrate examples of bio-derived crosslinking materials that may be formed from the reduced cis-aconitic acid molecule that may be synthesized according to the process previously described herein with respect to FIG. 5A. FIGS. 6A, 7A, 8A, 9A, and 10A illustrate that the reduced cis-aconitic acid molecule may be further modified with one of a variety of different functional groups that are used to cross-link or cure polymers, like PDMS. FIGS. 6B, 7B, 8B, 9B, and 10B illustrate examples of bio-derived crosslinking materials that may be formed from the reduced trans-aconitic acid molecule that may be synthesized according to the process previously described herein with respect to FIG. 5B. FIGS. 6B, 7B, 8B, 9B, and 10B illustrate that the reduced trans-aconitic acid molecule may be further modified with one of a variety of different functional groups that are used to cross-link or cure polymers, like PDMS.

Figure 6A:
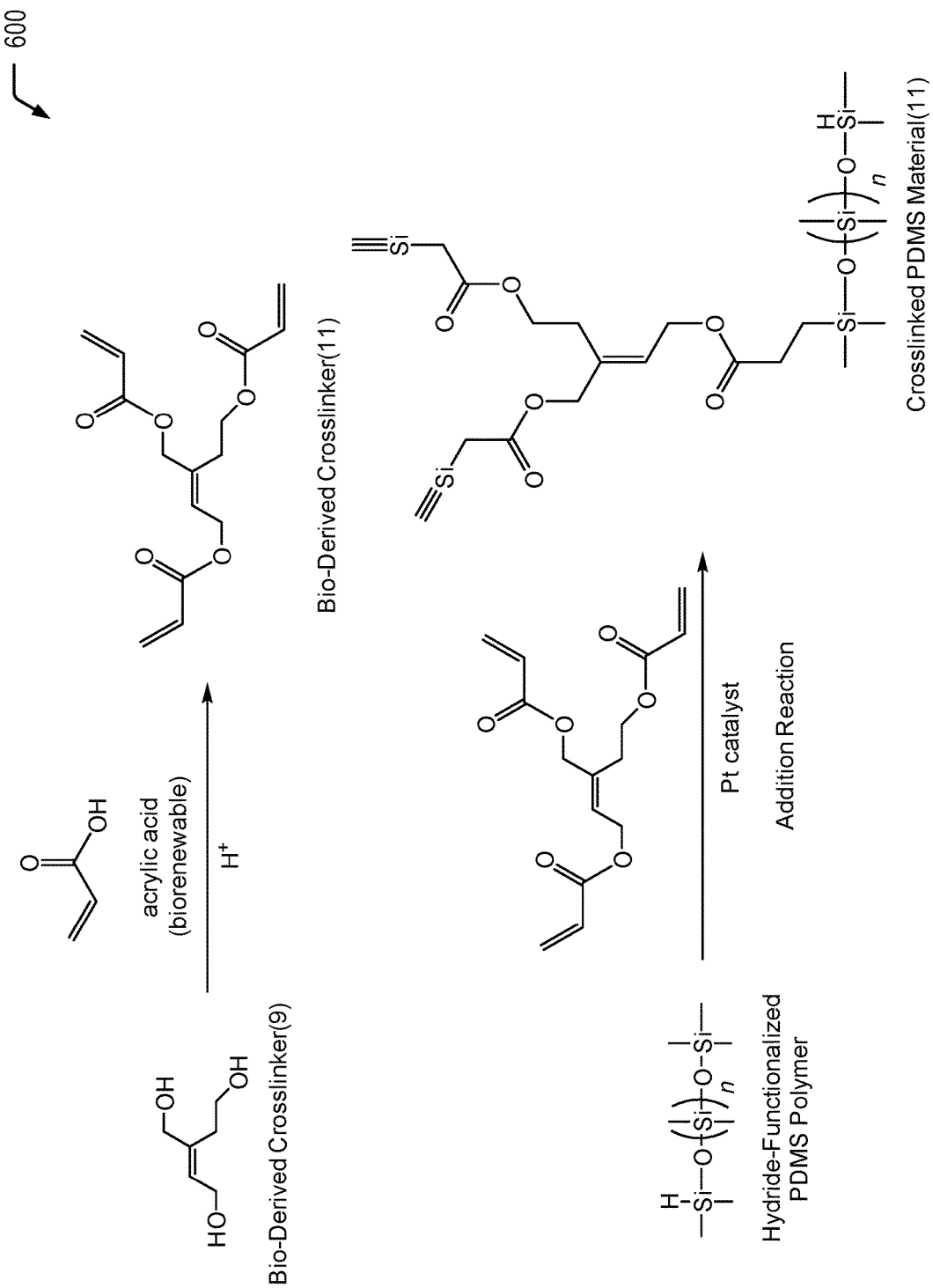
FIG. 6A is a chemical reaction diagram illustrating a process of forming a crosslinked PDMS material using a bio-derived crosslinking material having multiple vinyl groups that is formed from the bio-derived crosslinking material of FIG. 5A, according to one embodiment.

Referring to FIG. 6A, a chemical reaction diagram 600 illustrates a particular embodiment of a process of utilizing the reduced cis-aconitic acid molecule of FIG. 5A to form a bio-derived crosslinking material (identified as "Bio-Derived Crosslinker(11)" in FIG. 6A) that includes multiple acrylate groups. FIG. 6A further illustrates that the bio-derived crosslinking material may be utilized to form a crosslinked polymeric material (e.g., a crosslinked PDMS material), according to one embodiment.

The first chemical reaction depicted at the top of FIG. 6A illustrates that the reduced cis-aconitic acid molecule of FIG. 5A may be reacted with acrylic acid via acid-(or base-) catalyzed condensation reaction to form a crosslinker with multiple acrylate groups. Alternatively, acryloyl chloride may be formed from the acrylic acid, and may be used in place of acrylic acid along with an amine which may be pyridine or triethylamine. The acrylic acid may be formed from biorenewable resource(s).

As a prophetic example, the reduced cis-aconitic acid molecule (1 equiv.), acrylic acid (4.5-5.0 equiv.), catalyticp-toluenesulfonic acid (or other catalysts such as sulfonic acids, sulfuric acid, phosphoric acid, hydrogen sulfates, dihydrogen phosphates, phosphonic acid esters, or dialkyl tin dioxides) or a Lewis base such as dimethylaminopyridine (DMAP), and a suitable amount of toluene (or other water-azeotrope forming solvents) may be added to a reaction vessel and heated under azeotropic distillation conditions (e.g., refluxing using a Dean-Stark apparatus) until water is no longer removed from the reaction. The mixture may be cooled to room temperature, and the organic layer may be separated, rinsed with water, dried, and purified.

The second chemical reaction depicted at the bottom of FIG. 6A illustrates that the bio-derived crosslinking material having multiple acrylate groups may be utilized to form a crosslinked polymeric material. FIG. 6A illustrates a particular embodiment of an addition reaction that utilizes a platinum (Pt) catalyst. As a prophetic example, a hydride-functionalized siloxane may be blended with the bio-derived crosslinking material having multiple acrylate groups (1-20% w/w) and Pt catalyst, such as Speier's catalyst ($H_2PtCl_6$) or Karstedt's catalyst ($C_{24}H_{54}O_3Pt_2Si_6$), and are then mixed. An addition cure reaction via hydrosilation may be performed on the mixture.

FIG. 6A depicts an example in which all three acrylate groups of the bio-derived crosslinking material react in the addition reaction. Depending on the reaction conditions, all three acrylate groups may be used to crosslink the PDMS polymer or less than three acrylate groups may be used for crosslinking. To illustrate, by controlling the reaction conditions, catalyst type (other tin or platinum catalyst may be used), catalyst loading, and stoichiometry, a fraction of the acrylate groups can be used for PDMS crosslinking. The ability to control the number of acrylate groups that react may enable better control of the mechanical properties of the final polymer.

Thus, FIG. 6A illustrates an example of a process of forming a bio-derived crosslinking material having multiple acrylate groups from the reduced cis-aconitic acid molecule of FIG. 5A and utilizing the bio-derived crosslinking material to form a crosslinked polymeric material via an addition reaction. The bio-derived crosslinking material of FIG. 6A may be used to increase the biorenewable content of a resulting crosslinked polymeric material (e.g., a crosslinked PDMS material).

Figure 6B:
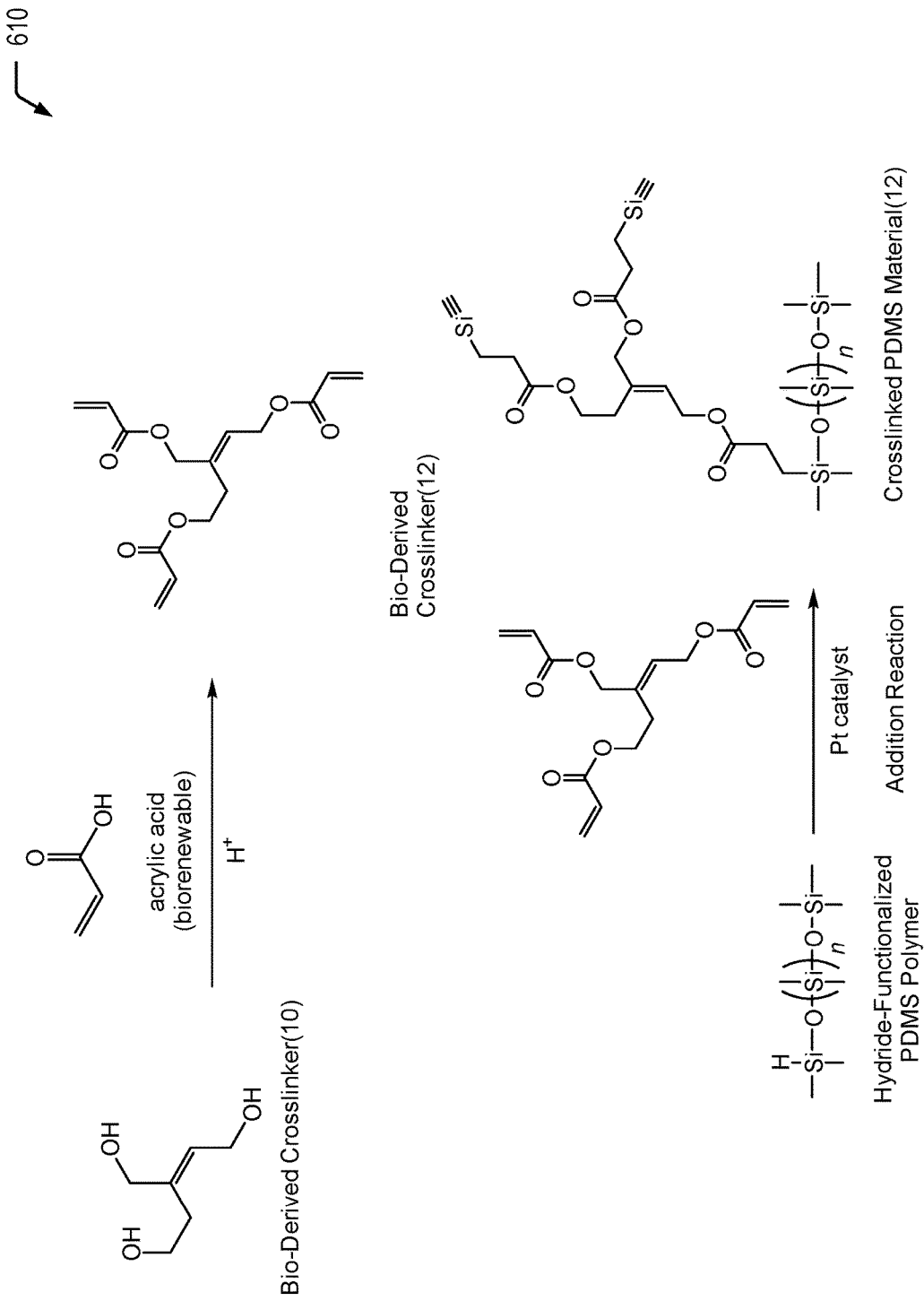
FIG. 6B is a chemical reaction diagram illustrating a process of forming a crosslinked PDMS material using a bio-derived crosslinking material having multiple vinyl groups that is formed from the bio-derived crosslinking material of FIG. 5B, according to one embodiment.

Referring to FIG. 6B, a chemical reaction diagram 610 illustrates a particular embodiment of a process of utilizing the reduced trans-aconitic acid molecule of FIG. 5B to form a bio-derived crosslinking material (identified as "Bio-Derived Crosslinker(12)" in FIG. 6B) that includes multiple acrylate groups. FIG. 6B further illustrates that the bio-derived crosslinking material may be utilized to form a crosslinked polymeric material (e.g., a crosslinked PDMS material), according to one embodiment.

The first chemical reaction depicted at the top of FIG. 6B illustrates that the reduced trans-aconitic acid molecule of FIG. 5B may be reacted with acrylic acid via an acid-(or base-) catalyzed condensation reaction to form a crosslinker with multiple acrylate groups. Alternatively, acryloyl chloride may be formed from the acrylic acid, and may be used in place of acrylic acid along with an amine which may be pyridine or triethylamine. The acrylic acid may be formed from biorenewable resource(s). The bio-derived crosslinking material depicted in FIG. 6B may be formed according to a process that is similar to the process previously described herein with respect to the bio-derived crosslinking material of FIG. 6A.

The second chemical reaction depicted at the bottom of FIG. 6B illustrates that the bio-derived crosslinking material having multiple acrylate groups may be utilized to form a crosslinked polymeric material. FIG. 6B illustrates a particular embodiment of an addition reaction that utilizes a platinum (Pt) catalyst. The crosslinked polymeric material depicted in FIG. 6B may be formed according to a process that is similar to the process previously described herein with respect to the crosslinked polymeric material of FIG. 6A.

FIG. 6B depicts an example in which all three acrylate groups of the bio-derived crosslinking material react in the addition reaction. Depending on the reaction conditions, all three acrylate groups may be used to crosslink the PDMS polymer or less than three acrylate groups may be used for crosslinking. To illustrate, by controlling the reaction conditions, catalyst type (other tin or platinum catalyst may be used), catalyst loading, and stoichiometry, a fraction of the acrylate groups can be used for PDMS crosslinking. The ability to control the number of acrylate groups that react may enable better control of the mechanical properties of the final polymer.

Thus, FIG. 6B illustrates an example of a process of forming a bio-derived crosslinking material having multiple acrylate groups from the reduced trans-aconitic acid molecule of FIG. 5B and utilizing the bio-derived crosslinking material to form a crosslinked polymeric material via an addition reaction. The bio-derived crosslinking material of FIG. 6B may be used to increase the biorenewable content of a resulting crosslinked polymeric material (e.g., a crosslinked PDMS material).

Figure 7A:
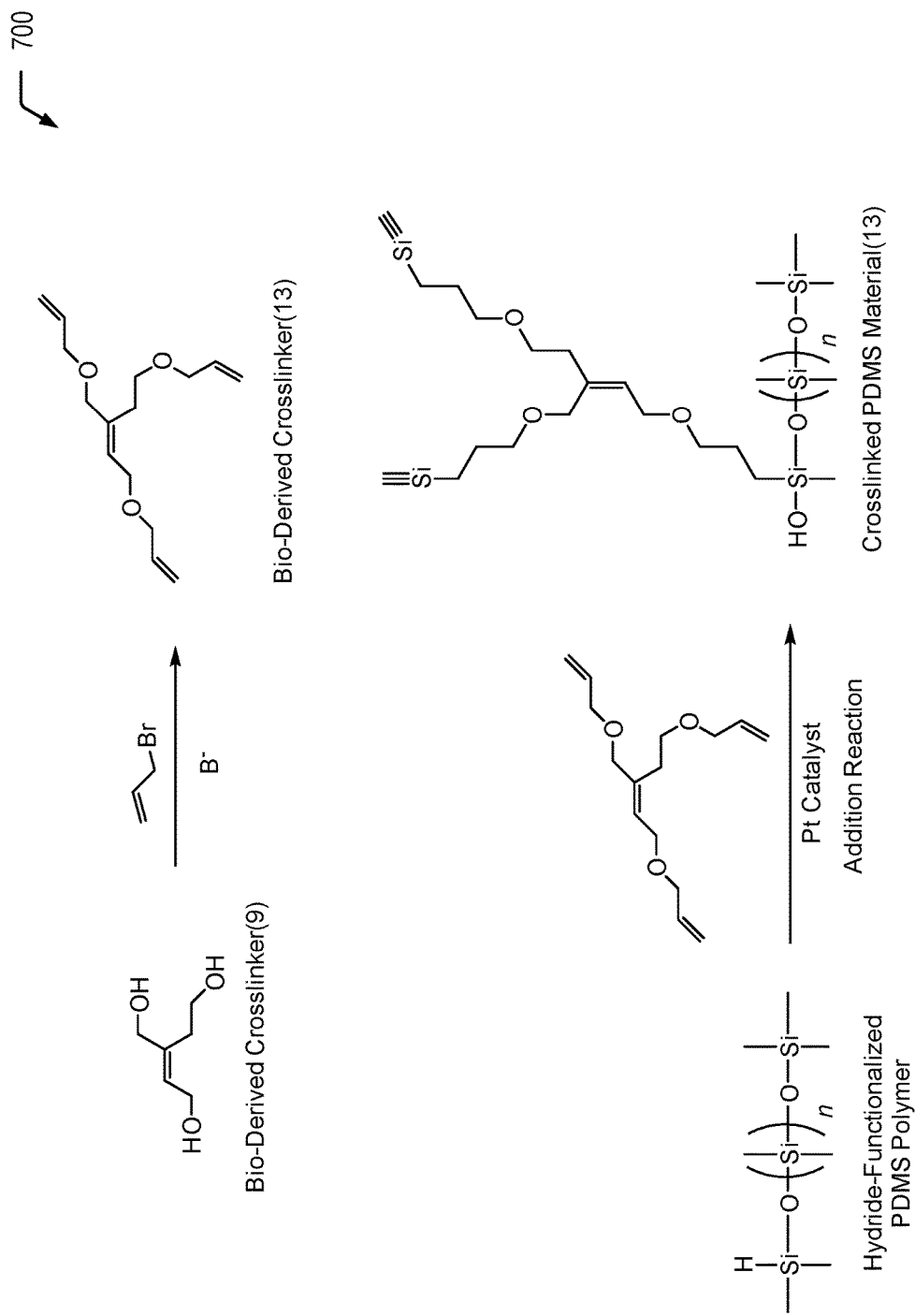
FIG. 7A is a chemical reaction diagram illustrating a process of forming a crosslinked PDMS material using a bio-derived crosslinking material having multiple vinyl groups that is formed from the bio-derived crosslinking material of FIG. 5A, according to one embodiment.

Referring to FIG. 7A, a chemical reaction diagram 700 illustrates a particular embodiment of a process of utilizing the reduced cis-aconitic acid molecule of FIG. 5A to form a bio-derived crosslinking material (identified as "Bio-Derived Crosslinker(13)" in FIG. 7A) that includes multiple vinyl groups. FIG. 7A further illustrates that the bio-derived crosslinking material may be utilized to form a crosslinked polymeric material (e.g., a crosslinked PDMS material), according to one embodiment.

The first chemical reaction depicted at the top of FIG. 7A illustrates that the reduced cis-aconitic acid molecule of FIG. 5A may be reacted with allyl bromide via a substitution reaction to form a crosslinker with multiple vinyl groups. In some cases, the allyl bromide may be synthesized in one step from biorenewable allyl alcohol. The bio-derived crosslinking material depicted in FIG. 7A may be formed according to a process that is similar to the process previously described herein with respect to the bio-derived crosslinking material of FIG. 1A.

The second chemical reaction depicted at the bottom of FIG. 7A illustrates that the bio-derived crosslinking material having multiple vinyl groups may be utilized to form a crosslinked polymeric material via an addition reaction. The cross-linking reaction depicted in FIG. 7A may be performed according to a process that is similar to the process previously described herein with respect to the bio-derived crosslinking material of FIG. 1A.

FIG. 7A depicts an example in which all three vinyl groups of the bio-derived crosslinking material react in the addition reaction. Depending on the reaction conditions, all three vinyl groups may be used to crosslink the PDMS polymer or less than three vinyl groups may be used for crosslinking. To illustrate, by controlling the reaction conditions, catalyst type (other tin or platinum catalyst may be used), catalyst loading, and stoichiometry, a fraction of the vinyl groups can be used for PDMS crosslinking. The ability to control the number of vinyl groups that react may enable better control of the mechanical properties of the final polymer.

Thus, FIG. 7A illustrates an example of a process of forming a bio-derived crosslinking material having multiple vinyl groups from the reduced cis-aconitic acid molecule of FIG. 5A and utilizing the bio-derived crosslinking material to form a crosslinked polymeric material via an addition reaction. The bio-derived crosslinking material of FIG. 7A may be used to increase the biorenewable content of a resulting crosslinked polymeric material (e.g., a crosslinked PDMS material).

Figure 7B:
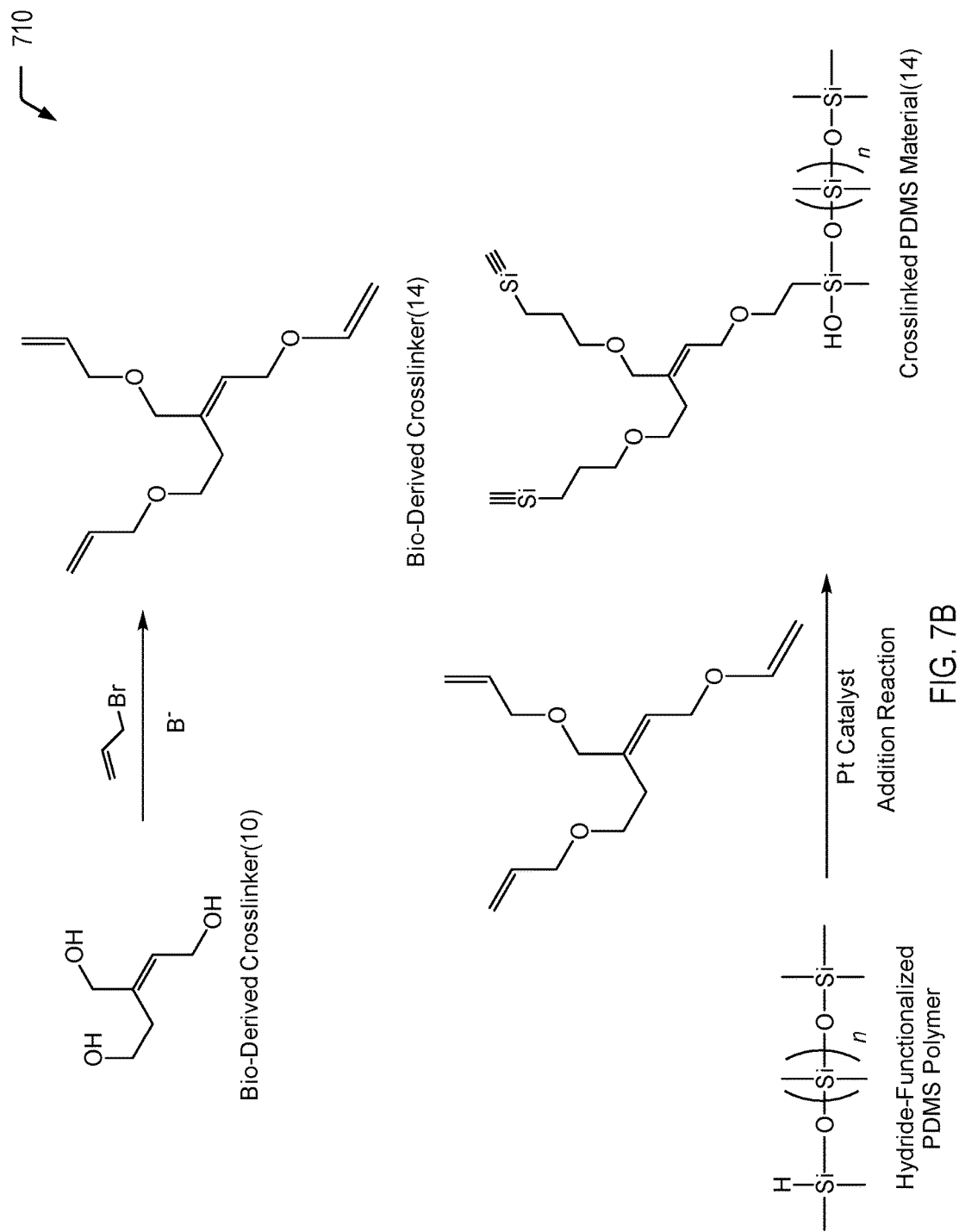
FIG. 7B is a chemical reaction diagram illustrating a process of forming a crosslinked PDMS material using a bio-derived crosslinking material having multiple vinyl groups that is formed from the bio-derived crosslinking material of FIG. 5B, according to one embodiment.

Referring to FIG. 7B, a chemical reaction diagram 710 illustrates a particular embodiment of a process of utilizing the reduced trans-aconitic acid molecule of FIG. 5B to form a bio-derived crosslinking material (identified as "Bio-Derived Crosslinker(14)" in FIG. 7B) that includes multiple vinyl groups. FIG. 7B further illustrates that the bio-derived crosslinking material may be utilized to form a crosslinked polymeric material (e.g., a crosslinked PDMS material), according to one embodiment.

The first chemical reaction depicted at the top of FIG. 7B illustrates that the reduced trans-aconitic acid molecule of FIG. 5B may be reacted with allyl bromide via a substitution reaction to form a crosslinker with multiple vinyl groups. In some cases, the allyl bromide may be synthesized in one step from biorenewable allyl alcohol. The bio-derived crosslinking material depicted in FIG. 7B may be formed according to a process that is similar to the process previously described herein with respect to the bio-derived crosslinking material of FIG. 1B.

The second chemical reaction depicted at the bottom of FIG. 7B illustrates that the bio-derived crosslinking material having multiple vinyl groups may be utilized to form a crosslinked polymeric material via an addition reaction. The cross-linking reaction depicted in FIG. 7B may be performed according to a process that is similar to the process previously described herein with respect to the bio-derived crosslinking material of FIG. 1B.

FIG. 7B depicts an example in which all three vinyl groups of the bio-derived crosslinking material react in the addition reaction. Depending on the reaction conditions, all three vinyl groups may be used to crosslink the PDMS polymer or less than three vinyl groups may be used for crosslinking. To illustrate, by controlling the reaction conditions, catalyst type (other tin or platinum catalyst may be used), catalyst loading, and stoichiometry, a fraction of the vinyl groups can be used for PDMS crosslinking. The ability to control the number of vinyl groups that react may enable better control of the mechanical properties of the final polymer.

Thus, FIG. 7B illustrates an example of a process of forming a bio-derived crosslinking material having multiple vinyl groups from the reduced trans-aconitic acid molecule of FIG. 5B and utilizing the bio-derived crosslinking material to form a crosslinked polymeric material via an addition reaction. The bio-derived crosslinking material of FIG. 7B may be used to increase the biorenewable content of a resulting crosslinked polymeric material (e.g., a crosslinked PDMS material).

Figure 8A:
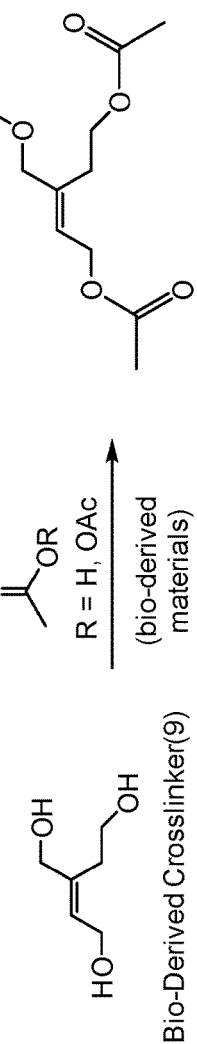
FIG. 8A is a chemical reaction diagram illustrating a process of forming a crosslinked PDMS material using a bio-derived crosslinking material having multiple acetate groups that is formed from the bio-derived crosslinking material of FIG. 5A, according to one embodiment.
Figure 8A:
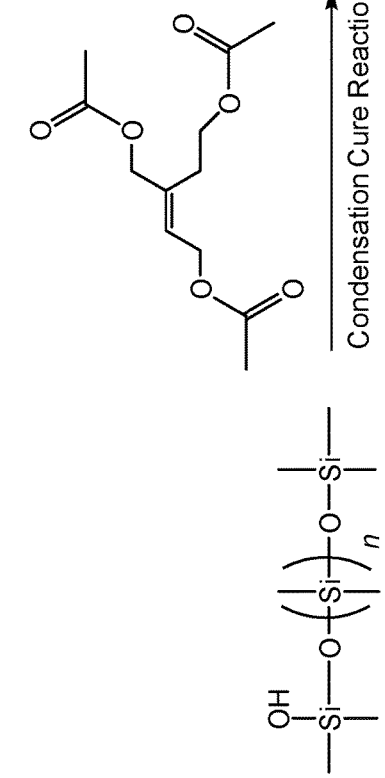

Referring to FIG. 8A, a chemical reaction diagram 800 illustrates a particular embodiment of a process of utilizing the reduced cis-aconitic acid molecule of FIG. 5A to form a bio-derived crosslinking material (identified as "Bio-Derived Crosslinker(15)" in FIG. 8A) that includes multiple acetate groups. FIG. 8A further illustrates that the bio-derived crosslinking material may be utilized to form a crosslinked polymeric material (e.g., a crosslinked PDMS material), according to one embodiment.

The first chemical reaction depicted at the top of FIG. 8A illustrates that the reduced cis-aconitic acid molecule of FIG. 5A may be reacted with acetic acid or acetic anhydride via an acylation reaction to form a crosslinker that includes multiple acetate groups. The bio-derived crosslinking material depicted in FIG. 8A may be formed according to a process that is similar to the process previously described herein with respect to the bio-derived crosslinking material of FIG. 2A.

The second chemical reaction depicted at the bottom of FIG. 8A illustrates that the bio-derived crosslinking material having multiple acetate groups may be utilized to form a crosslinked polymeric material via a condensation cure reaction. The cross-linking reaction depicted in FIG. 8A may be performed according to a process that is similar to the process previously described herein with respect to the bio-derived crosslinking material of FIG. 2A.

FIG. 8A depicts an example in which all three acetate groups of the bio-derived crosslinking material react in the condensation cure reaction. Depending on the reaction conditions, all three acetate groups may be used to crosslink the PDMS polymer or less than three acetate groups may be used for crosslinking. To illustrate, by controlling the reaction conditions, catalyst type (other tin or platinum catalyst may be used), catalyst loading, and stoichiometry, a fraction of the acetate groups can be used for PDMS crosslinking. The ability to control the number of acetate groups that react may enable better control of the mechanical properties of the final polymer.

Thus, FIG. 8A illustrates an example of a process of forming a bio-derived crosslinking material having multiple acetate groups from the reduced cis-aconitic acid molecule of FIG. 5A and utilizing the bio-derived crosslinking material to form a crosslinked polymeric material via a condensation cure reaction. The bio-derived crosslinking material of FIG. 8A may be used to increase the biorenewable content of a resulting crosslinked polymeric material (e.g., a crosslinked PDMS material).

Figure 8B:
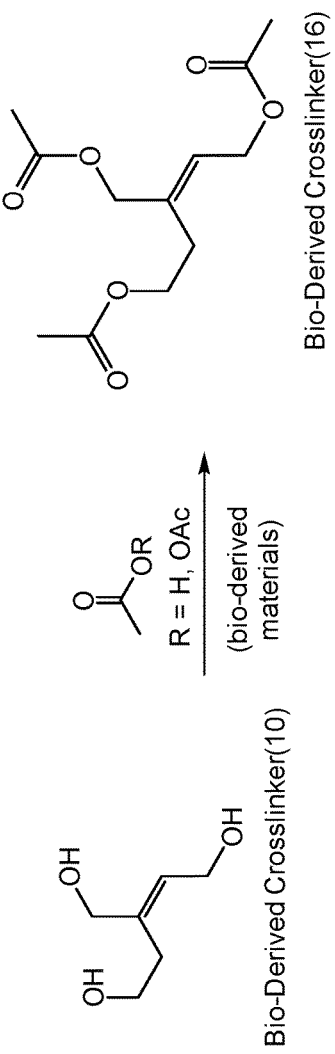
FIG. 8B is a chemical reaction diagram illustrating a process of forming a crosslinked PDMS material using a bio-derived crosslinking material having multiple acetate groups that is formed from the bio-derived crosslinking material of FIG. 5B, according to one embodiment.
Figure 8B:
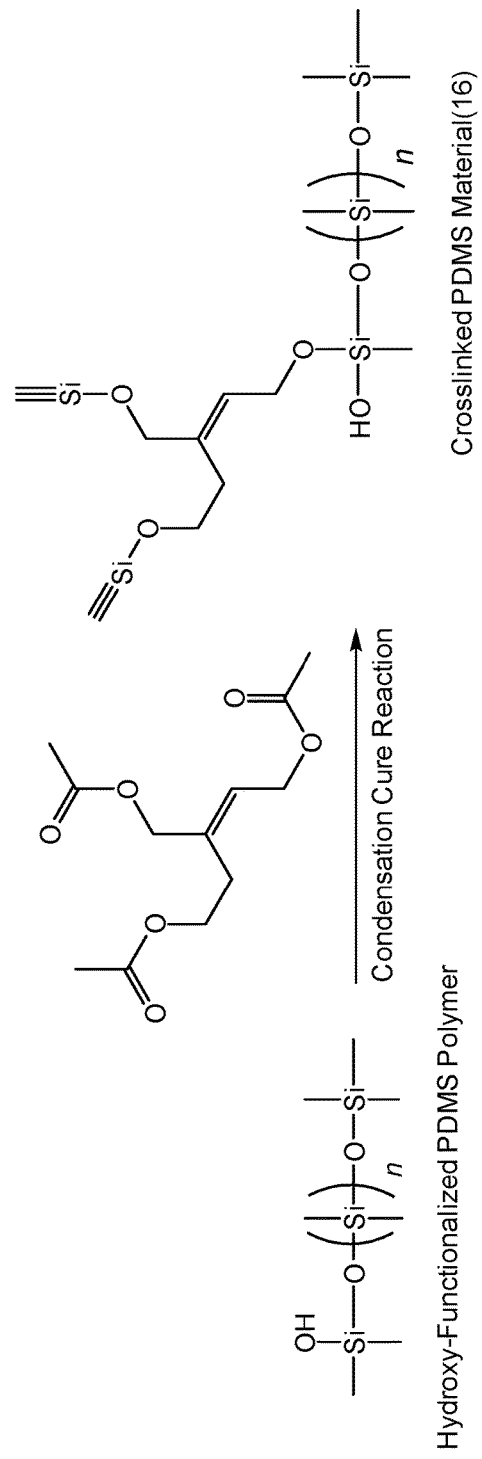

Referring to FIG. 8B, a chemical reaction diagram 810 illustrates a particular embodiment of a process of utilizing the reduced trans-aconitic acid molecule of FIG. 5B to form a bio-derived crosslinking material (identified as "Bio-Derived Crosslinker(16)" in FIG. 8B) that includes multiple acetate groups. FIG. 8B further illustrates that the bio-derived crosslinking material may be utilized to form a crosslinked polymeric material (e.g., a crosslinked PDMS material), according to one embodiment.

The first chemical reaction depicted at the top of FIG. 8B illustrates that the reduced trans-aconitic acid molecule of FIG. 5B may be reacted with acetic acid or acetic anhydride via an acylation reaction to form a crosslinker that includes multiple acetate groups. The bio-derived crosslinking material depicted in FIG. 8B may be formed according to a process that is similar to the process previously described herein with respect to the bio-derived crosslinking material of FIG. 2B.

The second chemical reaction depicted at the bottom of FIG. 8B illustrates that the bio-derived crosslinking material having multiple acetate groups may be utilized to form a crosslinked polymeric material via a condensation cure reaction. The cross-linking reaction depicted in FIG. 8B may be performed according to a process that is similar to the process previously described herein with respect to the bio-derived crosslinking material of FIG. 2B.

FIG. 8B depicts an example in which all three acetate groups of the bio-derived crosslinking material react in the condensation cure reaction. Depending on the reaction conditions, all three acetate groups may be used to crosslink the PDMS polymer or less than three acetate groups may be used for crosslinking. To illustrate, by controlling the reaction conditions, catalyst type (other tin or platinum catalyst may be used), catalyst loading, and stoichiometry, a fraction of the acetate groups can be used for PDMS crosslinking. The ability to control the number of acetate groups that react may enable better control of the mechanical properties of the final polymer.

Thus, FIG. 8B illustrates an example of a process of forming a bio-derived crosslinking material having multiple acetate groups from the reduced trans-aconitic acid molecule of FIG. 5B and utilizing the bio-derived crosslinking material to form a crosslinked polymeric material via a condensation cure reaction. The bio-derived crosslinking material of FIG. 8B may be used to increase the biorenewable content of a resulting crosslinked polymeric material (e.g., a crosslinked PDMS material).

Figure 9A:
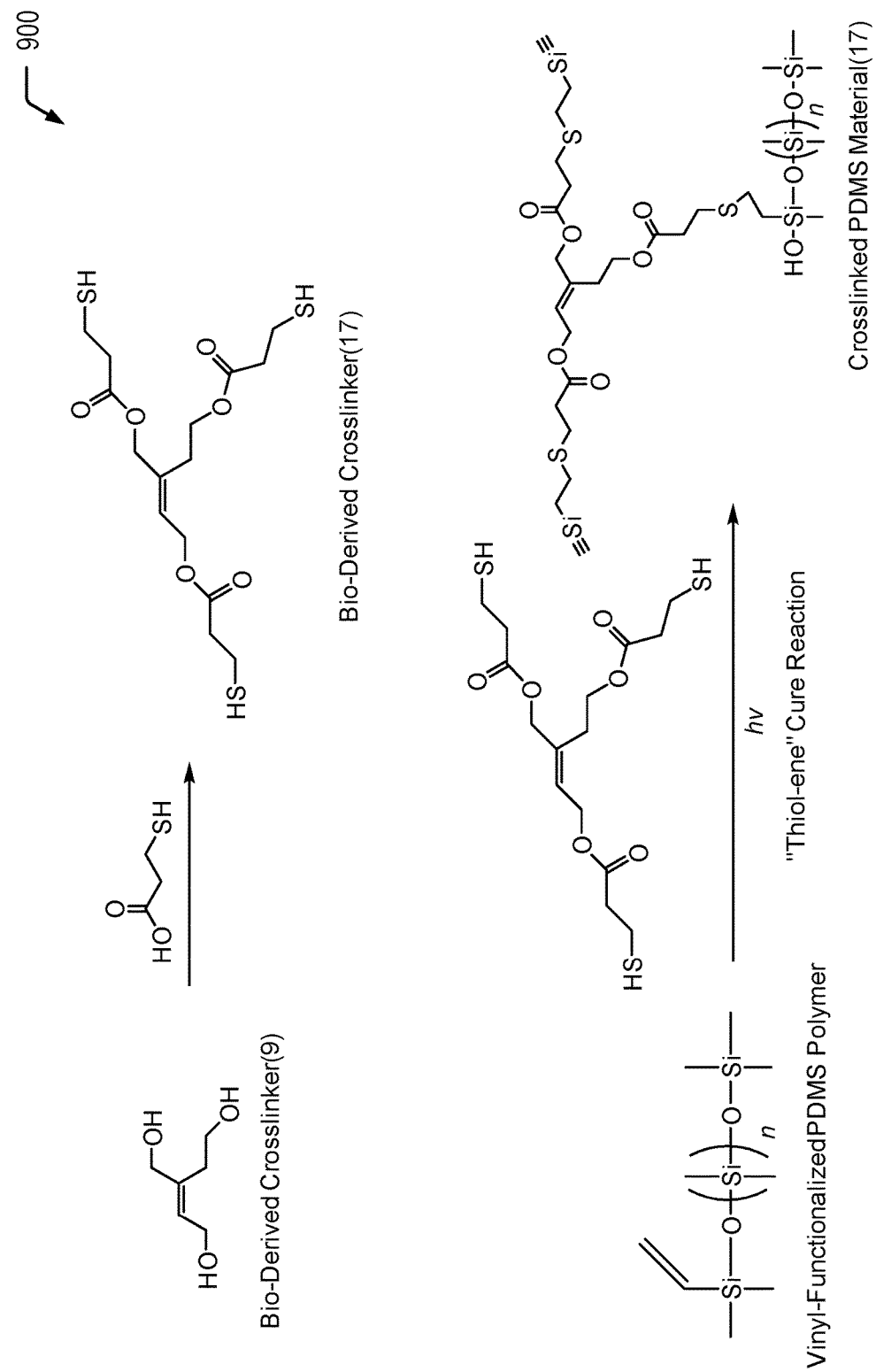
FIG. 9A is a chemical reaction diagram illustrating a process of forming a crosslinked PDMS material using a bio-derived crosslinking material having multiple thiol groups that is formed from the bio-derived crosslinking material of FIG. 5A, according to one embodiment.

Referring to FIG. 9A, a chemical reaction diagram 900 illustrates a particular embodiment of a process of utilizing the reduced cis-aconitic acid molecule of FIG. 5A to form a bio-derived crosslinking material (identified as "Bio-Derived Crosslinker(17)" in FIG. 9A) that includes multiple thiol (or mercapto) groups. FIG. 9A further illustrates that the bio-derived crosslinking material may be utilized to form a crosslinked polymeric material (e.g., a crosslinked PDMS material), according to one embodiment.

The first chemical reaction depicted at the top of FIG. 9A illustrates that the reduced cis-aconitic acid molecule of FIG. 5A may be reacted with ethyl mercaptoacetic acid via a condensation reaction (acid/base promoted) to form a bio-derived crosslinking material with multiple thiol (or mercapato) groups. The bio-derived crosslinking material depicted in FIG. 9A may be formed according to a process that is similar to the process previously described herein with respect to the bio-derived crosslinking material of FIG. 3A.

The second chemical reaction depicted at the bottom of FIG. 9A illustrates that the bio-derived crosslinking material with multiple thiol (or mercapato) groups may be utilized to form a crosslinked polymeric material via a thiol-ene cure reaction. The cross-linking reaction depicted in FIG. 9A may be performed according to a process that is similar to the process previously described herein with respect to the bio-derived crosslinking material of FIG. 3A.

FIG. 9A depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. To illustrate, by controlling the reaction conditions, catalyst type (other tin or platinum catalyst may be used), catalyst loading, and stoichiometry, a fraction of the thiol groups can be used for PDMS crosslinking. The ability to control the number of thiol groups that react may enable better control of the mechanical properties of the final polymer.

Thus, FIG. 9A illustrates an example of a process of forming a bio-derived crosslinking material having multiple thiol (or mercapto) groups from the reduced cis-aconitic acid molecule of FIG. 5A and utilizing the bio-derived crosslinking material to form a crosslinked polymeric material via a thiol-ene cure reaction. The bio-derived crosslinking material of FIG. 9A may be used to increase the biorenewable content of a resulting crosslinked polymeric material (e.g., a crosslinked PDMS material).

Figure 9B:
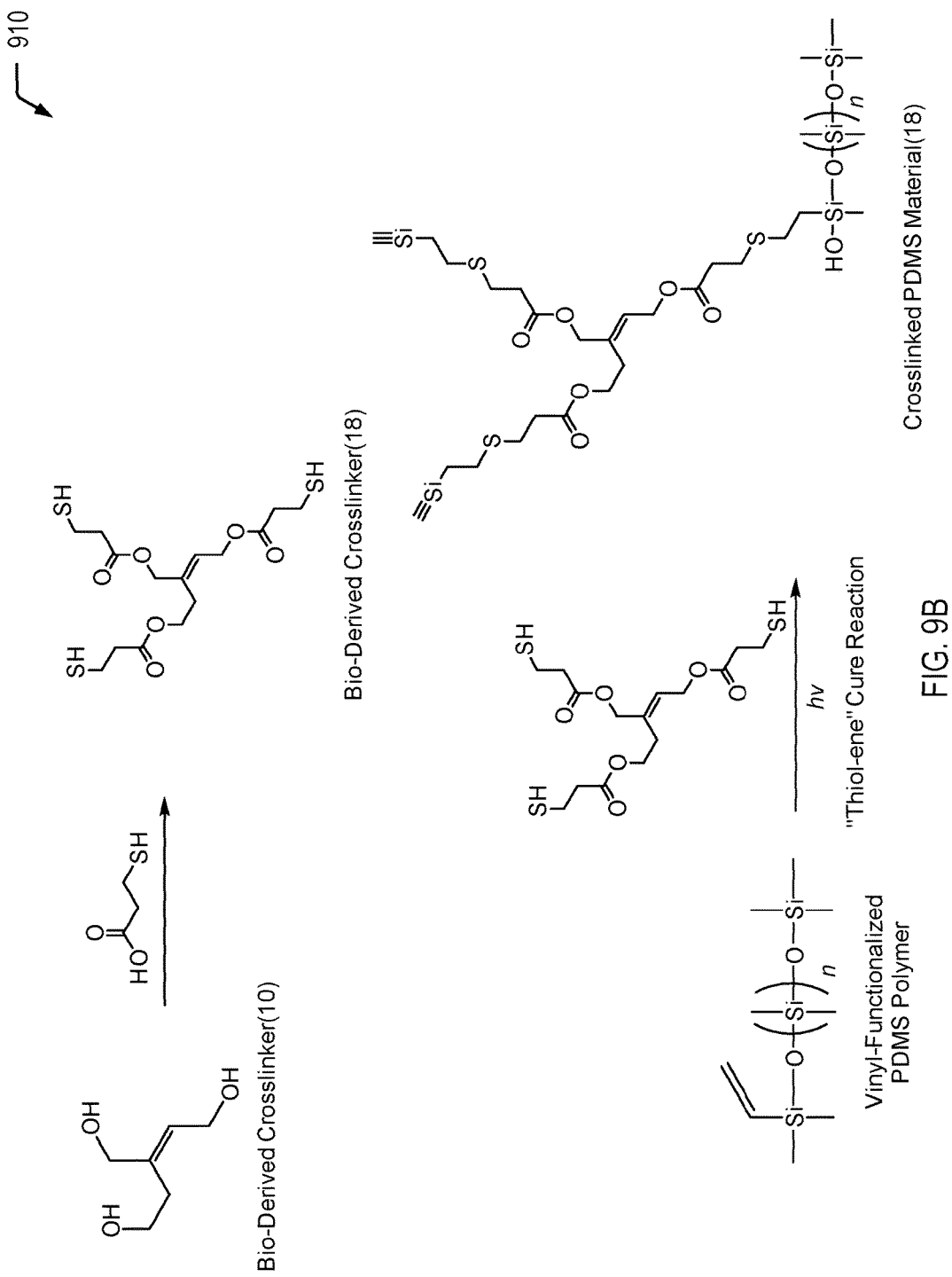
FIG. 9B is a chemical reaction diagram illustrating a process of forming a crosslinked PDMS material using a bio-derived crosslinking material having multiple thiol groups that is formed from the bio-derived crosslinking material of FIG. 5B, according to one embodiment.

Referring to FIG. 9B, a chemical reaction diagram 910 illustrates a particular embodiment of a process of utilizing the reduced trans-aconitic acid molecule of FIG. 5B to form a bio-derived crosslinking material (identified as "Bio-Derived Crosslinker(18)" in FIG. 9B) that includes multiple thiol (or mercapto) groups. FIG. 9B further illustrates that the bio-derived crosslinking material may be utilized to form a crosslinked polymeric material (e.g., a crosslinked PDMS material), according to one embodiment.

The first chemical reaction depicted at the top of FIG. 9B illustrates that the reduced trans-aconitic acid molecule of FIG. 5B may be reacted with ethyl mercaptoacetic acid via a condensation reaction (acid/base promoted) to form a bio-derived crosslinking material with multiple thiol (or mercapato) groups. The bio-derived crosslinking material depicted in FIG. 9B may be formed according to a process that is similar to the process previously described herein with respect to the bio-derived crosslinking material of FIG. 3B.

The second chemical reaction depicted at the bottom of FIG. 9B illustrates that the bio-derived crosslinking material with multiple thiol (or mercapato) groups may be utilized to form a crosslinked polymeric material via a thiol-ene cure reaction. The cross-linking reaction depicted in FIG. 9B may be performed according to a process that is similar to the process previously described herein with respect to the bio-derived crosslinking material of FIG. 3B.

FIG. 9B depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. To illustrate, by controlling the reaction conditions, catalyst type (other tin or platinum catalyst may be used), catalyst loading, and stoichiometry, a fraction of the thiol groups can be used for PDMS crosslinking. The ability to control the number of thiol groups that react may enable better control of the mechanical properties of the final polymer.

Thus, FIG. 9B illustrates an example of a process of forming a bio-derived crosslinking material having multiple thiol (or mercapto) groups from the reduced trans-aconitic acid molecule of FIG. 5B and utilizing the bio-derived crosslinking material to form a crosslinked polymeric material via a thiol-ene cure reaction. The bio-derived crosslinking material of FIG. 9B may be used to increase the biorenewable content of a resulting crosslinked polymeric material (e.g., a crosslinked PDMS material).

Figure 10A:
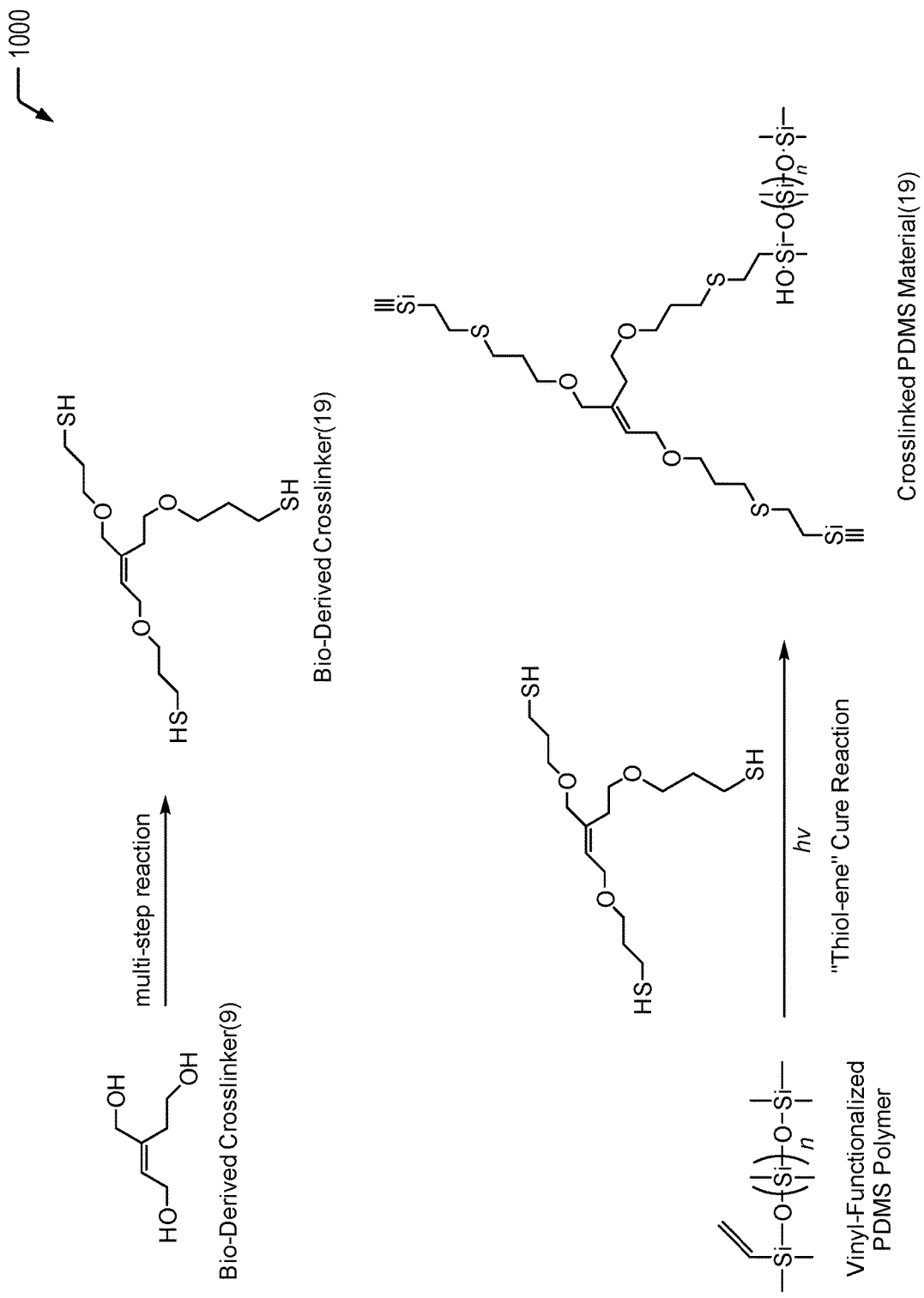
FIG. 10A is a chemical reaction diagram illustrating a process of forming a crosslinked PDMS material using a bio-derived crosslinking material having multiple thiol groups that is formed from the bio-derived crosslinking material of FIG. 5A, according to one embodiment.

Referring to FIG. 10A, a chemical reaction diagram 1000 illustrates a particular embodiment of a process of utilizing the reduced cis-aconitic acid molecule of FIG. 5A to form a bio-derived crosslinking material (identified as "Bio-Derived Crosslinker(19)" in FIG. 10A) that includes multiple thiol (or mercapto) groups. FIG. 10A further illustrates that the bio-derived crosslinking material may be utilized to form a crosslinked polymeric material (e.g., a crosslinked PDMS material), according to one embodiment.

The first chemical reaction depicted at the top of FIG. 10A illustrates that the reduced cis-aconitic acid molecule of FIG. 5A may be utilized to form a crosslinker with multiple thiol (or mercapto) groups via a multiple step reaction that includes the use of an acetate protected thiol bromopropane (commercially available) and substitution chemistry, then removing the protecting group. The bio-derived crosslinking material depicted in FIG. 9A may be formed according to a process that is similar to the process previously described herein with respect to the bio-derived crosslinking material of FIG. 4A.

The second chemical reaction depicted at the bottom of FIG. 10A illustrates that the bio-derived crosslinking material having multiple thiol groups may be utilized to form a crosslinked polymeric material via a thiol-ene cure reaction. The cross-linking reaction depicted in FIG. 10A may be performed according to a process that is similar to the process previously described herein with respect to the bio-derived crosslinking material of FIG. 4A.

FIG. 10A depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. To illustrate, by controlling the reaction conditions, catalyst type (other tin or platinum catalyst may be used), catalyst loading, and stoichiometry, a fraction of the thiol groups can be used for PDMS crosslinking. The ability to control the number of thiol groups that react may enable better control of the mechanical properties of the final polymer.

Thus, FIG. 10A illustrates an example of a process of forming a bio-derived crosslinking material having multiple thiol (or mercapto) groups from the reduced cis-aconitic acid molecule of FIG. 5A and utilizing the bio-derived crosslinking material to form a crosslinked polymeric material via a thiol-ene cure reaction. The bio-derived crosslinking material of FIG. 10A may be used to increase the biorenewable content of a resulting crosslinked polymeric material (e.g., a crosslinked PDMS material).

Figure 10B:
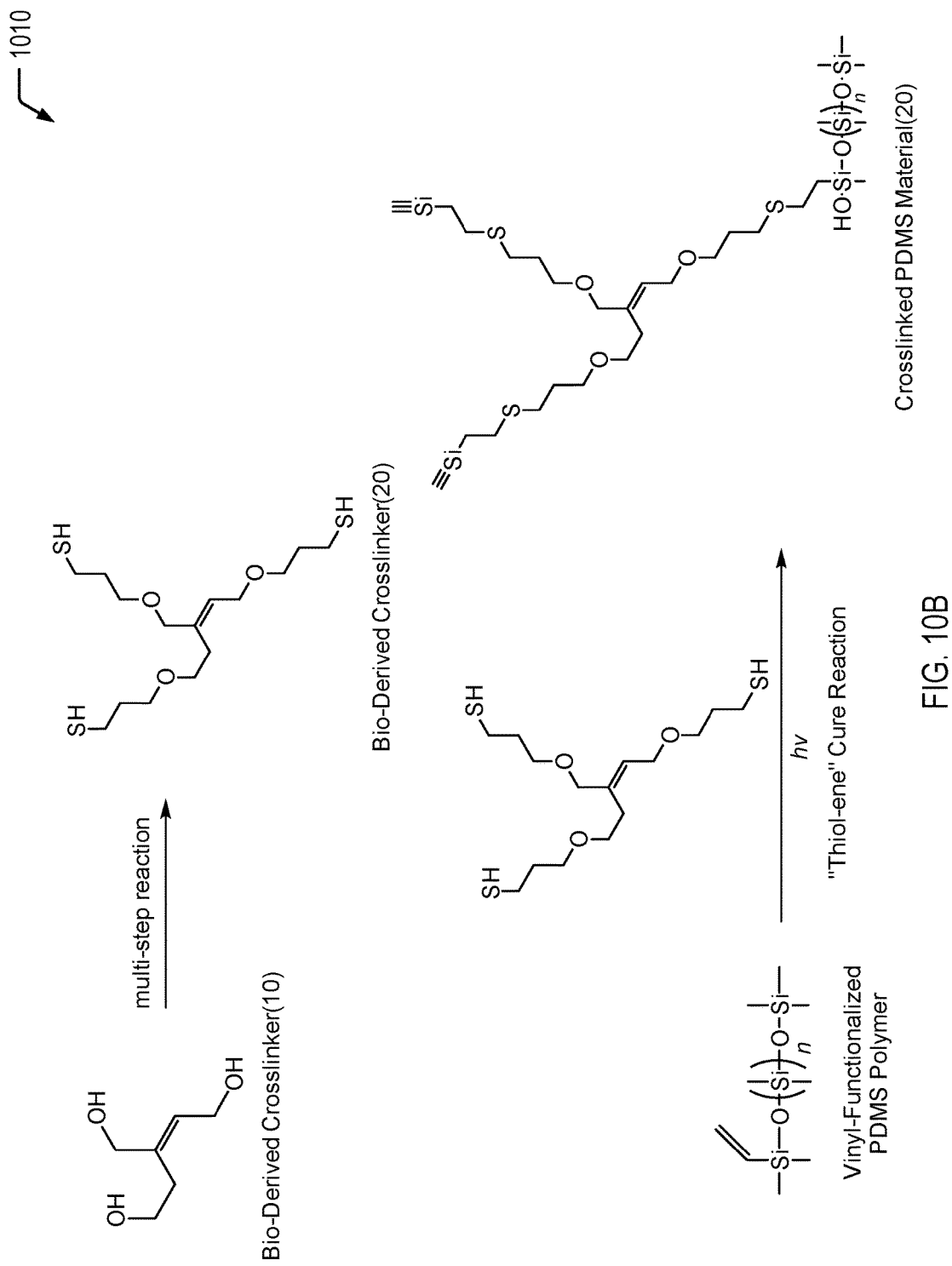
FIG. 10B is a chemical reaction diagram illustrating a process of forming a crosslinked PDMS material using a bio-derived crosslinking material having multiple thiol groups that is formed from the bio-derived crosslinking material of FIG. 5B, according to one embodiment.

Referring to FIG. 10B, a chemical reaction diagram 1010 illustrates a particular embodiment of a process of utilizing the reduced trans-aconitic acid molecule of FIG. 5B to form a bio-derived crosslinking material (identified as "Bio-Derived Crosslinker(20)" in FIG. 10B) that includes multiple thiol (or mercapto) groups. FIG. 10B further illustrates that the bio-derived crosslinking material may be utilized to form a crosslinked polymeric material (e.g., a crosslinked PDMS material), according to one embodiment.

The first chemical reaction depicted at the top of FIG. 10B illustrates that the reduced trans-aconitic acid molecule of FIG. 5B may be utilized to form a crosslinker with multiple thiol (or mercapto) groups via a multiple step reaction that includes the use of an acetate protected thiol bromopropane (commercially available) and substitution chemistry, then removing the protecting group. The bio-derived crosslinking material depicted in FIG. 10B may be formed according to a process that is similar to the process previously described herein with respect to the bio-derived crosslinking material of FIG. 4B.

The second chemical reaction depicted at the bottom of FIG. 10B illustrates that the bio-derived crosslinking material having multiple thiol groups may be utilized to form a crosslinked polymeric material via a thiol-ene cure reaction. The cross-linking reaction depicted in FIG. 10B may be performed according to a process that is similar to the process previously described herein with respect to the bio-derived crosslinking material of FIG. 4B.

FIG. 10B depicts an example in which all three thiol groups of the bio-derived crosslinking material react in the thiol-ene cure reaction. Depending on the reaction conditions, all three thiol groups may be used to crosslink the PDMS polymer or less than three thiol groups may be used for crosslinking. To illustrate, by controlling the reaction conditions, catalyst type (other tin or platinum catalyst may be used), catalyst loading, and stoichiometry, a fraction of the thiol groups can be used for PDMS crosslinking. The ability to control the number of thiol groups that react may enable better control of the mechanical properties of the final polymer.

Thus, FIG. 10B illustrates an example of a process of forming a bio-derived crosslinking material having multiple thiol (or mercapto) groups from the reduced trans-aconitic acid molecule of FIG. 5B and utilizing the bio-derived crosslinking material to form a crosslinked polymeric material via a thiol-ene cure reaction. The bio-derived crosslinking material of FIG. 10B may be used to increase the biorenewable content of a resulting crosslinked polymeric material (e.g., a crosslinked PDMS material).

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a bio-derived crosslinking material from biorenewable aconitic acid, the process comprising:
    initiating a chemical reaction to form a bio-derived crosslinking material corresponding to a tri-alcohol compound, wherein the chemical reaction includes a reduction reaction to convert carboxylic acid groups of a biorenewable aconitic acid molecule to hydroxyl groups.

2. The process of claim 1, further comprising initiating a second chemical reaction to form a second bio-derived crosslinking material, wherein the second chemical reaction includes converting the hydroxyl groups to acrylate groups, vinyl groups, acetate groups, or thiol groups.

3. The process of claim 1, wherein the biorenewable aconitic acid molecule includes a cis-aconitic acid isomer.

4. The process of claim 1, wherein the biorenewable aconitic acid molecule includes a trans-aconitic acid isomer.

5. The process of claim 1, wherein the biorenewable aconitic acid molecule includes a mixture of a cis-aconitic acid isomer and a trans-aconitic acid isomer.

6. The process of claim 1, wherein the tri-alcohol compound has the following structural formula:

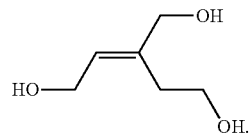

7. The process of claim 1, wherein the tri-alcohol compound has the following structural formula:

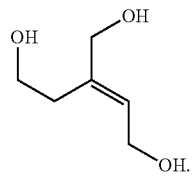

8. A process of forming a crosslinked polymeric material, the process comprising utilizing a tri-alcohol formed from a biorenewable aconitic acid molecule as a bio-derived crosslinking material to form the crosslinked polymeric material.

9. The process of claim 8, wherein the tri-alcohol is formed from the biorenewable aconitic acid molecule via a reduction reaction, the reduction reaction resulting in conversion of carboxylic acid groups of the biorenewable aconitic acid molecule to hydroxyl groups.

10. The process of claim 8, wherein the crosslinked polymeric material includes a crosslinked polydimethylsiloxane (PDMS) material that is formed from a hydride-functionalized PDMS material and the tri-alcohol via a condensation cure reaction.

11. The process of claim 8, wherein the tri-alcohol compound has the following structural formula:

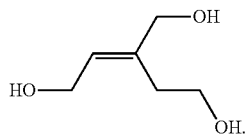

12. The process of claim 8, wherein the tri-alcohol compound has the following structural formula:

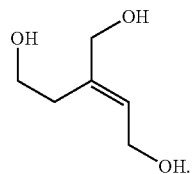

13. A crosslinked polydimethylsiloxane (PDMS) material formed by a process that comprises chemically reacting a functionalized PDMS material with a bio-derived crosslinking material that is derived from a biorenewable aconitic acid molecule, the bio-derived crosslinking material including multiple acrylate groups, acetate groups, or thiol groups.

14. The crosslinked PDMS material of claim 13, wherein the bio-derived crosslinking material includes multiple acrylate groups, and wherein the functionalized PDMS material includes a hydride-functionalized PDMS material.

15. The crosslinked PDMS material of claim 13, wherein the bio-derived crosslinking material includes multiple acetate groups, and wherein the functionalized PDMS material includes a hydroxy-functionalized PDMS material.

16. The crosslinked PDMS material of claim 13, wherein the bio-derived crosslinking material includes multiple thiol groups, and wherein the functionalized PDMS material includes a vinyl-functionalized PDMS material.

* * * * *